(12) United States Patent
Boenitz-Dulat et al.

(10) Patent No.: US 11,572,552 B2
(45) Date of Patent: Feb. 7, 2023

(54) SORTASE

(71) Applicant: Hoffmann-La Roche Inc., Little Falls, NJ (US)

(72) Inventors: Mara Boenitz-Dulat, Tutzing (DE); Martin Schatte, Karlsbad (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 229 days.

(21) Appl. No.: 17/127,765

(22) Filed: Dec. 18, 2020

(65) Prior Publication Data

US 2021/0238571 A1 Aug. 5, 2021

Related U.S. Application Data

(60) Division of application No. 16/144,841, filed on Sep. 27, 2018, now Pat. No. 10,900,026, which is a continuation of application No. PCT/EP2017/057247, filed on Mar. 28, 2017.

(30) Foreign Application Priority Data

Mar. 30, 2016 (EP) .................................... 16162916

(51) Int. Cl.
*C12N 9/52* (2006.01)
*A61K 47/65* (2017.01)

(52) U.S. Cl.
CPC ................ *C12N 9/52* (2013.01); *A61K 47/65* (2017.08); *C12Y 304/2207* (2013.01)

(58) Field of Classification Search
CPC ..... C12N 9/52; A61K 47/65; C12Y 304/2207
See application file for complete search history.

(56) References Cited

U.S. PATENT DOCUMENTS

| 4,150,149 | A | 4/1979 | Wolfsen et al. |
| 4,361,544 | A | 11/1982 | Goldenberg et al. |
| 4,444,744 | A | 4/1984 | Goldenberg et al. |
| 9,267,127 | B2 | 2/2016 | Liu et al. |
| 10,077,299 | B2 | 9/2018 | Song et al. |

FOREIGN PATENT DOCUMENTS

| WO | 2010/087994 A2 | 8/2010 |
| WO | 2010/099536 A2 | 9/2010 |
| WO | 2010/099536 A3 | 9/2010 |
| WO | 2013/003555 A1 | 1/2013 |
| WO | 2014/070865 A1 | 5/2014 |
| WO | 2014/175690 | 10/2014 |
| WO | 2015/042393 A2 | 3/2015 |

OTHER PUBLICATIONS

Biswas et al., "Sorting of LPXTG Peptides by Archetypal Sortase A: Role of Invariant Substrate Residues in Modulating the Enzyme Dynamics and Conformational Signature of a Productive Substrate" Biochemistry 53(15):2515-2524 ( 2014).
Chen et al., "A general strategy for the evolution of bond-forming enzymes using yeast display" Proceedings of the National Academy of Sciences 108(28):11399-11404 ( 2011).
Clancy, K., et al., "Sortase transpeptidases: Insights into mechanism, substrate specificity, and inhibition" Biopolymers 94(4):385-396 (Jun. 30, 2010).
Comfort et al., "A Comparative Genome Analysis Identifies Distinct Sorting Pathways in Gram-Positive Bacteria" Infection and Immunity 72(5):2710-2722 ( 2004).
Dennig et al., "OmniChange: The Sequence Independent Method for Simultaneous Site-Saturation of Five Codons" PLoS One 6(10):e26222 ( 2011).
Dramsi et al., "Sorting sortases: a nomenclature proposal for the various sortases of Gram-positive bacteria" Research in Microbiology 156:289-297 ( 2005).
Hatfield et al., "Antiangiogenic therapy in acute myelogenous leukemia: targeting of vascular endothelial growth factor and interleukin 8 as possible antileukemic strategies" Current Cancer Drug Targets 5:229-248 ( 2005).
Herberman et al., "Immunodiagnosis of Cancer" The Clinical Biochemistry of Cance, American Association of Clinical Chemists:347 ( 1979).
Ilangovan et al., "Structure of sortase, the transpeptidase that anchors proteins to the cell wall of *Staphylococcus aureus*" Proceedings of the National Academy of Sciences 98(11):6056-6061 ( 2001).
ISR and WIitten Opinion of PCT/EP2017/057247 (dated May 19, 2017).
Levary et al., "Protein-Protein Fusion Catalyzed by Sortase A" PLoS One 6(4 Suppl e18342):1-6 ( 2011).
Li et al., "Irreversible Site-Specific Hydrazinolysis of Proteins by Use of Sortase" Angewandte Chemie International Edition in English 53:2198-2202 ( 2014).
Madej et al., "Engineering of an Anti-Epidermal Growth Factor Receptor Antibody to Single Chain format and Labeling by Sortase A-Mediated Protein Ligation" Biotechnology and Bioengineering 109(6):1461-1470 ( 2012).
Marvin et al., "Recombinant approacehs to IgG-like bispecific antibodies" Acta Pharmacologica Sinica 26(6):649-658 (Jun. 2005).
Meissner, P. et al. et al., "Transient gene expression: recombinant protein production with suspension-adapted HEK293-EBNA cells" Biotechnol Bioeng 75:197-203 ( 2001).
Mizukami et al., "Induction of interleukin-8 preserves the angiogenic response in HIF-1alpha-deficient colon cancer cells." Nature Medicine 11(9):992-997 ( 2005).
Pallen et al., "An embarrassment of sortases—a richness of substrates?" Trends in Microbiology 9(3):97-102 ( 2001).
Popp et al., "Making and Breaking Peptide Bonds: Protein Engineering Using Sortase" Angew. Chem. Int. Ed. 50:5024-5032 ( 2011).

(Continued)

*Primary Examiner* — Paul J Holland
(74) *Attorney, Agent, or Firm* — Nicole Fortuné

(57) ABSTRACT

Reported herein is a sortase comprising an amino acid sequence that is at least 90% identical to the amino acid sequence of SEQ ID NO: 11 and that comprises the mutations D101S and K137S.

5 Claims, No Drawings

Specification includes a Sequence Listing.

(56) References Cited

OTHER PUBLICATIONS

Ren et al., "Macrophage migration inhibitory factor stimulates angiogenic factor expression and correlates with differentiation and lymph node status in patients with esophageal squamous cell carcinoma." Annals of Surgery 242:55-63 ( 2005).
Ta et al., "Enzymatic Single-Chain Antibody Tagging A Universal Approach to Targeted Molecular Imaging and Cell Homing in Cardiovascular Disease" Circulation Research 109:365-373 ( 2011).
Ton-That et al., "Purification and Characterization of Sortase, the Transpeptidase that Cleaves Surface Proteins of *Staphylococcus aureus* at the LPXTG Motif" PNAS 96(22):12424-12429 (Oct. 26, 1999).
Tsukiji et al., "Sortase-Mediated Ligation: A Gift from Gram-Positive Bacteiia to Protein Engineering" ChemBioChem 10:787-798 ( 2009).
Vallböhmer et al., "Molecular determinants of cetuximab efficacy" Journal of clinical oncology 23(15):3536-44 ( 2005).
Yamamura et al., "Enhancement of Sortase A-Mediated Protein Ligation by Inducing a beta-Hairpin Structure around the Ligation Site" Chem. Commun. 47:4742-4744 ( 2011).

SORTASE

CROSS-REFERENCE TO RELATED APPLICATIONS

This application is a divisional of U.S. application Ser. No. 16/144,841, filed Sep. 27, 2018 which is a continuation of International Patent Application No. PCT/EP2017/057247, having an international filing date of Mar. 28, 2017, which claims benefit under 35 U.S.C. § 119 to European Patent Application No. 16162916.7, filed on Mar. 30, 2016 which are incorporated herein by reference in their entirety

SEQUENCE LISTING

This application contains a Sequence Listing submitted via EFS-Web and hereby incorporated by reference in its entirety. Said ASCII copy, created on Dec. 15, 2020, is named Sequence_Listing.txt and is 48,617 bytes in size.

BACKGROUND OF INVENTION

The current invention is in the field of sortase. Herein is reported a sortase that has improved enzymatic activity and methods of using the same in transamidation reactions.

Sortase A (SrtA) is a membrane bound enzyme which attaches proteins covalently to the bacterial cell wall. The specific recognition motif on the SrtA substrate is LPXTG, whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthetized peptides to recombinantly expressed proteins.

In WO 2010/087994 methods for ligation and uses thereof are reported. Recombinant approaches to IgG-like bispecific antibodies are reported by Marvin, J. S., et al. (Acta Pharmacol. Sinica 26 (2005) 649-658). In WO 2013/003555 the use of sortases to install click chemistry handles for protein ligation is reported.

Levary, D. A., et al., report protein-protein fusion catalyzed by Sortase A (PLOS ONE 6 (2011)). Engineering of an anti-epidermal growth factor receptor antibody to single chain format and labeling by sortase A-mediated protein ligation is reported by Madej, M. P., et al. (Biotechnol. Bioeng. 109 (2012) 1461-1470). Ta, H. T., et al., report enzymatic single-chain antibody tagging as a universal approach to targeted molecular imaging and cell homing in cardiovascular diseases (Cir. Res. 109 (2011) 365-373). Popp, M., et al., report making and breaking peptide bonds—protein engineering using sortase (Angew. Chem. Int. Ed. Eng. 50 (2011) 5024-5032). Engineered proteins with high affinity for DOTA chelates are reported in WO 2010/099536.

Different efforts to block the revers reactions of Sortase have been reported. Yamamura, Y., et al. (Chem. Commun. 47 (2011) 4742-4744) reported enhancement of sortase A-mediated protein ligation by inducing a beta-hairpin structure around the ligation site by introducing a β-hairpin around the recognition site of the substrate.

Sorting of LPXTG peptides by archetypal sortase A, role of invariant substrate residues in modulating the enzyme dynamics and conformational signature of a productive substrate was reported by Biswas, T., et al. (Biochem. 53 (2014) 2515-2524).

Li, Y. M., et al. report irreversible site-specific hydrazinolysis of proteins by use of Sortase (Angew. Chem. Int. Ed. Engl. 53 (2014) 2198-2202).

In U.S. Pat. No. 9,267,127 evolved sortases exhibiting enhanced reaction kinetics and/or altered substrate preferences and methods for using such evolved bond-forming enzymes are reported. Therein a sortase comprising an amino acid sequence that is at least 90% identical to the amino acid sequence of *Staphylococcus aureus* Sortase A, wherein the amino acid sequence of the sortase comprises two or more mutations selected from the group consisting of P94S, P94R, E106G, F122Y, K154R, D160N, D165A, G174S, K190E, and K196T is reported. The same evolved sortase is used in WO 2014/70865 and WO 2015/42393.

Chen, I., et al. report a general strategy for the evolution of bond-forming enzymes using yeast display (Proc. Natl. Acad. Sci. USA 108 (2011) 11399-11404).

SUMMARY OF THE INVENTION

Herein is reported a *Staphylococcus aureus* Sortase A with improved catalytic properties. It has been found that by introducing the mutations D160S and K196S into wild-type *Staphylococcus aureus* Sortase A of SEQ ID NO: 01 the enzymatic properties of the sortase can be improved (e.g. the term D160S denotes that the amino acid residue D at position 160 of SEQ ID NO: 01 is replaced by/mutated to the amino acid residue S). The herein reported sortase has an enzymatic activity that is about 5-times the enzymatic activity of wild-type Sortase A from *Staphylococcus aureus* (determined in an assay as reported herein).

One aspect as reported herein is a sortase comprising an amino acid sequence that is at least 90% identical to the amino acid sequence of SEQ ID NO: 11, wherein the amino acid sequence comprises the mutations D101S and K137S, and wherein the sortase has a higher enzymatic activity in a sortase mediated coupling reaction (determined in an assay as reported herein) as a sortase that has the amino acid sequence of SEQ ID NO: 11.

One aspect as reported herein is a sortase comprising an amino acid sequence that is at least 90% identical to the amino acid sequence of *Staphylococcus aureus* Sortase A of SEQ ID NO: 01, wherein the amino acid sequence comprises the mutations D160S and K196S (resulting in a Sortase A that has the amino acid sequence of SEQ ID NO: 02).

That is one aspect as reported herein is a polypeptide that has sortase activity, i.e. that catalyzes the formation of a peptide bond between a first compound comprising the amino acid sequence LPXTG (SEQ ID NO: 21) and a second compound comprising at di- or tri-glycine at its N-terminus, that is at least 90% identical to the amino acid sequence of *Staphylococcus aureus* Sortase A of SEQ ID NO: 01, wherein the amino acid sequence comprises the mutations D160S and K196S (resulting in a Sortase A that has the amino acid sequence of SEQ ID NO: 02).

In one embodiment the sortase/polypeptide of SEQ ID NO: 01 further comprises one or more mutations selected from the group of mutations consisting of A61E, A61T, E106G, N107W, F144L, and G167E.

In one embodiment the sortase/polypeptide comprises the mutations
i) D160S, K196S, and E106G (SEQ ID NO: 03), or
ii) D160S, K196S, and N107W (SEQ ID NO: 04), or
iii) D160S, K196S, and F144L (SEQ ID NO: 05), or
iv) D160S, K196S, and G167E (SEQ ID NO: 06), or
v) D160S, K196S, N107W, and F144L (SEQ ID NO: 07), or
vi) D160S, K196S, F144L, and G167E (SEQ ID NO: 08), or
vii) D160S, K196S, N107W, and G167E (SEQ ID NO: 09), or
viii) D160S, K196S, N107W, F144L, and G167E (SEQ ID NO: 10).

One aspect as reported herein is a sortase/polypeptide that has the amino acid sequence of SEQ ID NO: 02, or SEQ ID NO: 03, or SEQ ID NO: 04, or SEQ ID NO: 05, or SEQ ID NO: 06, or SEQ ID NO: 07, or SEQ ID NO: 08, or SEQ ID NO: 09, or SEQ ID NO: 10.

One aspect as reported herein is a sortase comprising an amino acid sequence that is at least 90% identical to the amino acid sequence of a shortened *Staphylococcus aureus* Sortase A of SEQ ID NO: 11, wherein the amino acid sequence comprises the mutations D101S and K137S (resulting in a shortened Sortase A that has the amino acid sequence of SEQ ID NO: 12).

That is one aspect as reported herein is a polypeptide that has sortase activity, i.e. that catalyzes the formation of a peptide bond between a first compound comprising the amino acid sequence LPXTG (SEQ ID NO: 21) and a second compound comprising at di- or tri-glycine at its N-terminus, that is at least 90% identical to the amino acid sequence of *Staphylococcus aureus* Sortase A of SEQ ID NO: 11, wherein the amino acid sequence comprises the mutations D101S and K137S (resulting in a Sortase A that has the amino acid sequence of SEQ ID NO: 02).

In one embodiment the sortase/polypeptide of SEQ ID NO: 12 further comprises one or more mutations selected form the group of mutations consisting of A2E, A2T, E47G, N48W, F85L, and G108E.

In one embodiment the sortase/polypeptide comprises the mutations
i) D101S, K137S, and E47G (SEQ ID NO: 13), or
ii) D101S, K137S, and N48W (SEQ ID NO: 14), or
iii) D101S, K137S, and F85L (SEQ ID NO: 15), or
iv) D101S, K137S, and G108E (SEQ ID NO: 16), or
v) D101S, K137S, N48W, and F85L (SEQ ID NO: 17), or
vi) D101S, K137S, F85L, and G108E (SEQ ID NO: 18), or
vii) D101S, K137S, N48W, and G108E (SEQ ID NO: 19), or
viii) D101S, K137S, N48W, F85L, and G108E (SEQ ID NO: 20).

One aspect as reported herein is a sortase/polypeptide comprising an amino acid sequence of SEQ ID NO: 12, or SEQ ID NO: 13, or SEQ ID NO: 14, or SEQ ID NO: 15, or SEQ ID NO: 16, or SEQ ID NO: 17, or SEQ ID NO: 18, or SEQ ID NO: 19, or SEQ ID NO: 20.

One aspect as reported herein is a sortase/polypeptide that has the amino acid sequence of SEQ ID NO: 12, or SEQ ID NO: 13, or SEQ ID NO: 14, or SEQ ID NO: 15, or SEQ ID NO: 16, or SEQ ID NO: 17, or SEQ ID NO: 18, or SEQ ID NO: 19, or SEQ ID NO: 20.

One aspect as reported herein is a method for producing a polypeptide comprising the step of incubating together i) a first polypeptide comprising a sortase recognition sequence, ii) a second polypeptide comprising a sortase acceptor sequence, and iii) a sortase/polypeptide as reported herein, and thereby producing the polypeptide.

In one embodiment the method comprises the following steps
incubating together
i) a first polypeptide comprising the amino acid sequence LPXTG (SEQ ID NO: 21), wherein X can be any amino acid residue,
ii) a second polypeptide that comprises a sortase acceptor sequence selected from I) a glycinyl compound at its N-terminus, II) an oligoglycine at its N-terminus, III) a cysteine amino acid residue followed by one to three glycine amino acid residues at its N-terminus, or IV) a lysine amino acid residue within its 5 N-terminal amino acid residues,
iii) a sortase/polypeptide as reported herein, and
recovering the polypeptide from the reaction mixture and thereby producing the polypeptide.

In one embodiment the method is for the enzymatic conjugation of two polypeptides.

In one embodiment the first polypeptide comprises within 20 amino acid residues of its C-terminus the amino acid sequence LPXTG (SEQ ID NO: 21), wherein X can be any amino acid residue. In one embodiment the first polypeptide comprises within 20 amino acid residues of its C-terminus the amino acid sequence LPETG (SEQ ID NO: 22).

In one embodiment the second polypeptide has at its N-terminus the amino acid sequence GG (SEQ ID NO: 23), GGG (SEQ ID NO: 24), CGG (SEQ ID NO: 25), or KGG (SEQ ID NO: 26).

In one embodiment first polypeptide and the second polypeptide are independently of each other selected from the group consisting of an antibody variable domain, an antibody heavy chain Fab-fragment, an antibody Fc-region, a tag, a label, a toxin, and a non-sortase polypeptide.

DETAILED DESCRIPTION OF THE INVENTION

The invention is based at least in part on the finding that the enzymatic activity of a sortase can be improved by mutating the amino acid residues D160 and K196 of the full length wild-type Sortase A of *Staphylococcus aureus* that has the amino acid sequence of SEQ ID NO: 01 or residues D101 and K137 of the shortened Sortase A of *Staphylococcus aureus* that has the amino acid sequence of SEQ ID NO: 11, respectively, both to serine.

I. DEFINITIONS

As used herein, the amino acid positions given are the respective (sequential) positions in the referred to amino acid sequence.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Furthermore, even if not disclosed specifically all possible variations, combinations and permutations of the aspects and embodiments as reported herein are enclosed and form specific embodiments of the invention. This encompasses the introduction of one or more limitations, elements, clauses, descriptive terms, etc., from one or more of the claims or from relevant portions of the description into another claim. For example, any claim can be modified to include one or more limitations found in any other claim that is dependent thereon. Furthermore, where the claims recite a compound or a composition, it is to be understood that methods of using the compound or composition for any of the purposes disclosed herein are included, and methods of making the compound or composition according to any of the methods of making disclosed herein or other methods known in the art are included, unless otherwise indicated or unless it would be evident to one of ordinary skill in the art that a contradiction or inconsistency would arise.

Where features are presented as lists it is to be understood that each subgroup of features as well as individual features are also disclosed, and any feature(s) can be removed from the group without extending the disclosure.

Where ranges are given the endpoints of the ranges are expressly included and also disclosed as individual values. Unless otherwise indicated or otherwise evident from the context and/or the understanding of one of ordinary skill in the art, values that are expressed as ranges include and disclose all embodiments directed to any specific value within that range without the need to expressly name this specific value. Also unless otherwise indicated or otherwise evident from the context and/or the understanding of one of ordinary skill in the art, values expressed as ranges include any subrange within the given endpoints of the range, wherein the endpoints of the subrange are expressed to the same degree of accuracy as those of the range.

The term "mutation" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of a mutation as used herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, aib and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "tag" denotes a sequence of amino acid residues connected to each other via peptide bonds that has specific binding properties. In one embodiment the tag is an affinity or purification tag. In one embodiment the tag is selected from Arg-tag, His-tag, Flag-tag, 3×Flag-tag, Strep-tag, HA-tag, Nano-tag, SBP-tag, c-myc-tag, S-tag, SNUT-Tag, NusA, T7, thioredoxin, calmodulin-binding-peptide, cellulose-binding-domain, chitin-binding-domain, GST-tag, or MBP-tag (see, e.g., Amau, J., et al., Prot. Expr. Purif. 48 (2006) 1-13). In one embodiment the tag is selected from the group of tags consisting of SEQ ID NO: 27 (RRRRR), SEQ ID NO: 28 (RRRRRR), SEQ ID NO: 29 (HHHHHH), SEQ ID NO: 30 (KDHLIHNVHKEFHAHAHNK), SEQ ID NO: 31 (DYKDDDDK), SEQ ID NO: 32 (DYKDHDGDYKDH-DIDYKDDDDK), SEQ ID NO: 33 (AWRHPQFGG), SEQ ID NO: 34 (WSHPQFEK), SEQ ID NO: 35 (MDVEAWL-GAR), SEQ ID NO: 36 (MDVEAWLGARVPLVET), SEQ ID NO: 37 (MDEKTTGWRGGHVVEGLAGELEQLRAR-LEHHPQGQREP), SEQ ID NO: 38 (EQKLISEEDL), SEQ ID NO: 39 (KETAAAKFERQHMDS), SEQ ID NO: 40 (KRRWKKNFIAVSAANRFKKISSSGAL), SEQ ID NO: 41 (cellulose binding domain), SEQ ID NO: 42 (cellulose binding domain), SEQ ID NO: 43 (TNPGVSAWQVNTAY-TAGQLVTYNGKTYKCLQPHTSLAGWEP SNVPALWQLQ), SEQ ID NO: 44 (GST-tag), and SEQ ID NO: 45 (MBP-tag).

The term "position" denotes the location of an amino acid residue in the amino acid sequence of a polypeptide. Positions may be numbered sequentially, for example in polypeptides, or according to an established format, for example the EU index of Kabat for antibody numbering. In any case the first amino acid residue has the number 1.

The term "sortase" denotes a polypeptide that has sortase activity, i.e., a sortase is an enzyme that catalyzes a transpeptidation reaction conjugating (the C-terminus of) a first polypeptide to the N-terminus of a second polypeptide via transamidation. The term includes full-length sortases, e.g. full-length naturally occurring sortases, fragments thereof that have sortase activity, and modified, e.g. mutated, variants thereof. A person skilled in the art will readily be able to determine whether or not a given polypeptide has sortase activity, e.g. by incubating, i.e. contacting, the polypeptide in question with a first and second polypeptide one comprising a sortase recognition motif and one a sortase acceptor motif under conditions suitable for transpeptidation and determining whether the respective transpeptidation reaction product is formed. A sortase polypeptide can comprise any number of amino acid residues as long as it has sortase activity. This does not denote that the sortase has to have the same activity as a wild-type sortase. It is sufficient that sortase activity is detectable with a suitable assay. The term sortase encompasses all known sortases such as e.g. sortase A, sortase B, sortase C, and sortase D type sortases. In one embodiment the sortase is a sortase A. This sortase A can be from any bacterial species or strain. In one embodiment the sortase is sortase A of *Staphylococcus aureus*. The amino acid sequence of wild-type sortase A of *S. aureus* is known and a representative sequence has been deposited e.g. under accession number AF162687 disclosing the coding sequence (frame 1 reading) of SEQ ID NO: 01:

```
MKKWTNRLMT IAGVVLILVA AYLFAKPHID NYLHDKDKE

KIEQYDKNVK EQASKDKKQQ AKPQIPKDKS KVAGYIEIPD

ADIKEPVYPG PATPEQLNRG VSFAEENESL DDQNISIAGH

TFIDRPNYQF TNLKAAKKGS MVYFKVGNET RKYKMTSIRD

VKPTDVGVLD EQKGKDKQLT LITCDDYNEK TGVWEKRKIF

VATEVK
``` or under accession number WP_000759359.1 disclosing the coding sequence of SEQ ID NO: 46:

```
MKKWTNRLMT IAGVVLILVA AYLFAKPHID NYLHDKDKE

KIEQYDKNVK EQASKDKKQQ AKPQIPKDKS KVAGYIEIPD

ADIKEPVYPG PATPEQLNRG VSFAEENESL DDQNISIAGH

TFIDRPNYQF TNLKAAKKGS MVYFKVGNET RKYKMTSIRD

VKPTDVEVLD EQKGKDKQLT LITCDDYNEK TGVWEKRKIF

VATEVK.
```

In one embodiment the sortase is Sortase A of *Streptococcus pyogenes*.

II. MUTATED SORTASE A

Herein is reported a *Staphylococcus aureus* Sortase A with improved catalytic properties. It has been found that by introducing the mutations D160S and K196S into wild-type *Staphylococcus aureus* Sortase A (SEQ ID NO: 01 to SEQ ID NO: 02) the enzymatic properties can be improved. The herein reported mutated sortase has an enzymatic activity that is about 5-times the enzymatic activity of wild-type Sortase A from *Staphylococcus aureus* using an assay as reported herein. A reference mutant known from the art with 6 mutations has only about 4-times increased activity in an assay as reported herein. It is also encompassed herein the same mutations at the respective positions in shortened versions of the wild-type Sortase A of *Staphylococcus aureus*. In the shortened version the same amino acid residues can be mutated although due to the difference in length (i.e. number of residues) of the amino acid sequence these have a different absolute position in the amino acid sequence.

Herein is provided a mutated Sortase A of *Staphylococcus aureus*. In some embodiments, the mutated sortase has improved catalytic properties, such as an improved (i.e. faster) reaction kinetics in that it catalyzes a transpeptidation reaction at a greater speed and/or turnover rate than the respective wild-type sortase. In some embodiments, the mutated sortase has an altered substrate specificity in that it binds a given substrate with improved (i.e. higher) or reduced (i.e. lower) affinity, or with improved (i.e. more specific) or reduced (i.e. less specific, more promiscuitive) specificity than the respective wild-type sortase.

The properties of the purified, double mutated sortase as reported herein are summarized in the following Table:

| | relative activity | relative stability | relative apparent "Km" for LPXTG | relative apparent "Km" for GG |
|---|---|---|---|---|
| Reference 1: wild-type (SEQ ID NO: 01) at 0.015 mg/ml | 100% | 100% | reference | reference |
| Reference 2: P94R/D160N/D165A/G167E/K190E/K196T from US 9,267,127 (SEQ ID NO: 52) at 0.0075 mg/ml | 432% | 82% | lower | higher |
| D160S/K196S as reported herein (SEQ ID NO: 02) at 0.0075 mg/ml | 525% | 80% | lower | higher |

The properties of individual mutated sortase as reported herein determined from crude cultivation supernatants are summarized in the following Table:

| | relative activity | relative stability | relative apparent "Km" for LPXTG | relative apparent "Km" for GG |
|---|---|---|---|---|
| D160S/K196S | 100% | 100% | 100% | 100% |
| D160S/K196S + E106G | 143% | 95% | 121% | 117% |
| D160S/K196S + N107W | 149% | 105% | 121% | 111% |
| D160S/K196S + N107W + E106G | 141% | 89% | 107% | 122% |
| D160S/K196S + F144L | 145% | 121% | 100% | 100% |
| D160S/K196S + G167E | 148% | 142% | 131% | 117% |
| D160S/K196S + A61E | 131% | 74% | 100% | 97% |
| D160S/K196S + A61T | 129% | 68% | 97% | 78% |
| D160S/K196S + N107W + G167E | 192% | 142% | 166% | 94% |
| D160S/K196S + F144L + G167E | 161% | 111% | 166% | 83% |
| D160S/K196S + N107W + F144L | 153% | 121% | 134% | 94% |
| D160S/K196S + N107W + F144L + G167E | 201% | 168% | 197% | 94% |

A change in the relative activity to more than 100% compared to the wild-type enzyme denotes that the mutant has a higher initial velocity.

A change in the relative stability to more than 100% compared to the wild-type enzyme denotes that after heat treatment more enzyme remains active, whereas a change to less than 100% denotes that after heat treatment less enzyme remains active.

A change in the relative apparent "Km" for LPXTG (polypeptide comprising the sortase recognition motif) to more than 100% compared to the wild-type enzyme denotes that the mutant has a higher activity at low substrate concentration compared to the activity at high substrate concentrations, whereas a change to less than 100% denotes that the mutant has a lower activity at low substrate concentration compared to the activity at high substrate concentrations.

A change in the relative apparent "Km" for GG (polypeptide comprising the sortase acceptor motif) to more than 100% compared to the wild-type enzyme denotes that the mutant has a higher activity at low substrate concentration compared to the activity at high substrate concentrations, whereas a change to less than 100% denotes that the mutant has a lower activity at low substrate concentration compared to the activity at high substrate concentrations.

One aspect as reported herein is a sortase comprising an amino acid sequence that is at least 90% identical to the amino acid sequence of *Staphylococcus aureus* Sortase A of SEQ ID NO: 01 and that comprises the mutations D160S and K196S.

In one embodiment the sortase of SEQ ID NO: 01 further comprises one or more mutations selected from the group of mutations consisting of A61E, A61T, E106G, N107W, F144L, and G167E.

In one embodiment the sortase comprises the mutations
 i) D160S, K196S, and E106G (SEQ ID NO: 03), or
 ii) D160S, K196S, and N107W (SEQ ID NO: 04), or
 iii) D160S, K196S, and F144L (SEQ ID NO: 05), or
 iv) D160S, K196S, and G167E (SEQ ID NO: 06), or
 v) D160S, K196S, N107W, and F144L (SEQ ID NO: 07), or
 vi) D160S, K196S, F144L, and G167E (SEQ ID NO: 08), or
 vii) D160S, K196S, N107W, and G167E (SEQ ID NO: 09), or
 viii) D160S, K196S, N107W, F144L, and G167E (SEQ ID NO: 10).

Herein is provided a mutated sortase comprising an amino acid sequence that is homologous to the amino acid sequence of the respective wild-type Sortase A of *Staphylococcus aureus* (SEQ ID NO: 01) or a fragment thereof (SEQ ID NO: 11). In some embodiments the amino acid sequence of the mutated sortase comprises the mutations D160S and K196S in SEQ ID NO: 01, or D101S and K137S in SEQ ID NO: 11. In one embodiment the mutated sortase comprises one or more further mutations. For example, the mutated sortase may comprise 2, 3, 4, 5, 6, 7, 8, 9, 10, 11, 12, 13, 14, 15, 16, 17, 18, 19, or 20 mutations with respect to SEQ ID NO: 01 (resulting in an identity of more than 90%), or 2, 3, 4, 5, 6, 7, 8, 9, 10, 11, 12, 13, or 14 mutations with respect to SEQ ID NO: 11 (resulting in an identity of more than 90%). In one embodiment the mutated sortase comprises 2, 3, 4, 5, 6, or 7 mutations with respect to a sortase that has the amino acid sequence of SEQ ID NO: 01 or a sortase fragment that has the amino acid sequence of SEQ ID NO: 11. In one embodiment the amino acid sequence of the mutated sortase is at least 90% identical, at least 95% identical, at least 98% identical, at least 99% identical, or more than 99% identical to the sequence of SEQ ID NO: 01. In one embodiment the amino acid sequence of the mutated sortase is at least 90% identical, at least 95% identical, at least 98% identical, or more than 98% identical to the sequence of SEQ ID NO: 11.

In one embodiment the (mutated) sortase as reported herein has a $K_M$ value for the polypeptide comprising the sortase recognition motif that is less than the $K_M$ of the corresponding parent sortase of SEQ ID NO: 01 or SEQ ID NO: 11, respectively, for the same polypeptide, and a $K_M$ value for the polypeptide comprising the sortase acceptor sequence that is greater than the $K_M$ of the corresponding parent sortase of SEQ ID NO: 01 or SEQ ID NO: 11, respectively, for the same polypeptide.

In one embodiment the (mutated) sortase as reported herein has a $K_M$ value for the polypeptide comprising the sortase recognition motif that is at least the same, or at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, or at least 50-fold less than the $K_M$ of the corresponding parent sortase of SEQ ID NO: 01 or SEQ ID NO: 11, respectively, for the same polypeptide. In one embodiment the (mutated) sortase as reported herein has a $K_M$ value for the polypeptide comprising the sortase acceptor sequence that is at least the same, not more than 2-fold, not more than 5-fold, not more than 10-fold, or not more than 20-fold greater than the $K_M$ of the parent sortase for the same polypeptide.

Aspects of the invention are also variants of the mutated sortases as reported herein that maintain the enzymatic properties of the mutated sortases as reported herein.

A variant amino acid sequence departs from a parent or reference amino acid sequence. Amino acid substitutions may be made on the basis of similarity in polarity, charge, solubility, hydrophobicity, hydrophilicity, helix-forming properties and/or amphipathic properties and the resulting variants are screened for enzymatic activity with a suitable assay, such as that reported in European patent application EP14198535. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. In certain embodiments, conservative substitutions may be made, according to the Table below. Amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

| aliphatic amino acid residues | non-polar | G, A, P |
| --- | --- | --- |
| | | I, L, V |
| | polar, non-charged | C, S, T, M |
| | | N, Q |
| | polar, charged | D, E |
| | | K, R |
| aromatic | | H, F, W, Y |

In certain embodiments homologous substitution may occur, which is a substitution or replacement of like amino acids, such as basic for basic, acidic for acidic, polar for polar, and hydrophobic for hydrophobic amino acids, for example. Non-homologous substitutions can be introduced to a parent or reference sequence, such as from one class of residue to another (e. g. a non-hydrophobic to a hydrophobic amino acid), or substituting a naturally occurring amino acid with an unnatural amino acid or non-classical amino acid replacements.

Sortase Activity Assay:

Purified sortase or variant thereof was mixed with a glucose dehydrogenase containing the LPETG motif (20 μM) and a biotin derivative containing N-terminal glycines (20 μM) in 50 mM Tris buffer pH 7.5 containing 200 mM NaCl. The reaction mixture was incubated at 37° C. for two hours. The reaction was stopped by addition of a 10- to 40-fold excess of inhibition buffer (50 mM Tris, pH 7.5, 200 mM NaCl, 10 mM CaCl2, 5 mM iodoacetamide). The stopped reaction mixture was centrifuged for 10 min. at 5000×g. The supernatant (50 μL) was added to 100 μL of 50 mM Tris buffer (pH 7.5) comprising 200 mM NaCl, 10 mM CaCl2 and added on a streptavidin coted multi titer plate and incubated for 30 min. at 30° C. at 200 rpm. Thereafter the multi titer plate was washed five times with 300 μL washing buffer each (50 mM Tris, pH 7.5, 200 mM NaCl, 10 mM CaCl2, 5 mg/mL BSA, 0.1% Triton X-100). Thereto 150 µL test buffer (0.2 M sodium citrate, pH 5.8, 0.3 g/L 4-nitrosoanilin, 1 mM CaCl2, 30 mM glucose) was added.

The kinetic of the reporter enzyme is measured over a time period of 5 min. at 620 nm. The activity of the reporter enzyme is proportional to the amount of immobilized enzyme, which is proportional to the amount of biotinylated enzyme and this is proportional to the activity of the sortase.

III. ENZYMATIC CONJUGATION USING SORTASE A

A covalent conjugate comprising two in vivo not covalently associated entities can be obtained in vitro by using the enzyme sortase, especially sortase A.

Transamidases in general catalyze the formation of a peptide bond (amide bond) between an acyl donor and a nucleophilic acyl acceptor. In order to form a peptide bond the acyl acceptor has to contain a NH2-CH2-moiety. Gram-positive bacteria include the following genera: *Actinomyces, Bacillus, Bifidobacterium, Cellulomonas, Clostridium, Corynebacterium, Micrococcus, Mycobacterium, Nocardia, Staphylococcus, Streptococcus* and *Streptomyces*.

Sortases have been classified into 4 classes, designated A, B, C, and D, based on sequence alignment and phylogenetic analysis of 61 sortases from gram-positive bacterial genomes (Dramsi, S., et al., Res. Microbiol. 156 (2005) 289-297). These classes correspond to the following subfamilies, into which sortases have also been classified by Comfort and Clubb (Comfort, D. and Clubb, R. T., Infect. Immun. 72 (2004) 2710-2722): Class A (Subfamily 1), Class B (Subfamily 2), Class C (Subfamily 3), Class D (Subfamilies 4 and 5). The aforementioned references disclose numerous sortases and recognition motifs (see also Pallen, M. J., et al., Trends Microbiol. 9 (2001) 97-101). With this information a person skilled in the art can assign a sortase to the correct class based on its sequence and/or other characteristics such as those described in Drami (supra).

Sortase A (SrtA) is a membrane bound enzyme that has transamidase activity. It has been identified and isolated from gram-positive bacteria. In vivo Sortase A attaches proteins covalently to the bacterial cell wall. The specific recognition motif on the SrtA substrate is LPXTG (SEQ ID NO: 21), whereby the enzyme cleaves between the residues threonine and glycine. The recognition motif on the peptidoglycan is a pentaglycine motif. It has been shown that a triglycine and even a diglycine motif on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthetized peptides to recombinantly expressed proteins.

Many gram-positive bacteria use a sortase to covalently anchor a variety of surface proteins including virulence factors to their cell wall (peptidoglycan). Sortases are membrane associated enzymes. The wild-type *Staphylococcus aureus* sortase A (SrtA) is a polypeptide of 206 amino acids with an N-terminal membrane-spanning region. In a first step, sortase A recognizes substrate proteins that contain a LPXTG (SEQ ID NO: 21) amino acid sequence motif and cleaves the amide bond between the Thr and Gly by means of an active-site Cys. This peptide cleaving reaction results in a sortase A-substrate thioester intermediate. In a second step the thioester acyl-enzyme intermediate is resolved by nucleophilic attack of an amino group of an oligoglycine containing second substrate polypeptide (corresponding to the pentaglycine unit of peptidoglycan in *S. aureus*) leading to a covalently linked cell wall protein and the regeneration of sortase A. In the absence of oligoglycine nucleophiles, the acyl-enzyme intermediate can be hydrolyzed by a water molecule.

Sortase-mediated ligation/conjugation has begun to be applied for a variety of protein engineering and bioconjugation purposes. This technique enables the introduction of natural and synthetic functionalities into LPXTG-tagged recombinant or chemically synthesized polypeptides. Examples include the covalent attachment of oligoglycine derivatized polymers (e.g. PEG), fluorophores, vitamins (e.g. biotin and folate), lipids, carbohydrates, nucleic acids, synthetic peptides and proteins (e.g. GFP) (see e.g. Tsukiji, S. and Nagamune, T., ChemBioChem 10 (2009) 787-798; Popp, M. W. L. and Ploegh, H. L., Angew. Chem. Int. Ed. Engl. 50 (2011) 5024-5032).

For the enzymatic conjugation a soluble truncated sortase A lacking the membrane-spanning region (SrtA; amino acid residues 60-206 of *Staphylococcus aureus* SrtA) can be used (SEQ ID NO: 11; see also Ton-That, H., et al., Proc. Natl. Acad. Sci. USA 96 (1999) 12424-12429; Ilangovan, H., et al., Proc. Natl. Acad. Sci. USA 98 (2001) 6056-6061).

The sortase A-mediated reaction results in the ligation of species containing a sortase recognition sequence (sortase motif) with those bearing a sortase acceptor sequence (e.g. one or more N-terminal glycine residues). The sortase recognition sequence can be an amino acid sequence LPXTG (SEQ ID NO: 21), but can also different therefrom. However, a drawback of using such sequences as acyl donors is that the transfer of the LPXT (SEQ ID NO: 47) unit to a nucleophilic acyl acceptor liberates a stoichiometric amount of a corresponding fragment containing at least one N-terminal glycine residue. The liberated glycine-containing fragment competes with the intended acyl acceptor for the enzymatic intermediate and works against the progress of the enzymatic ligation reaction. Additionally the hydrolytic cleavage of the enzymatic intermediate as well as the LPXTG containing substrate, although a relatively slow process, competes with the reaction. In the beginning of the use of the sortase-mediated reaction useful levels of ligation could only be obtained using concentrations of at least 5 mM of the acyl donor comprising the sortase-motif.

In certain embodiments the sortase-motif has the amino acid sequence LPX1TX2 (SEQ ID NO: 48), wherein i) X1 is selected from the group of amino acid residues consisting of D, E, A, N, Q, K, and R, and ii) X2 is selected from the group of amino acid residues consisting of alanine and glycine. In certain embodiments the sortase-motif is LPX1TG (SEQ ID NO: 49). In certain embodiments the sortase-motif is LPX1TA (SEQ ID NO: 50). X1 has the meaning as outlined before.

Sortase fragments having sortase transamidation activity can be used in the methods as reported herein. Sortase fragments can be identified by producing fragments of the parental sortase, for example, by recombinant techniques or proteolytic digestion, and determining the rate of peptide bond formation, i.e. ligation. The fragment can comprise about 80% of amino acid sequence of the parent sortase, about 70%, about 60%, about 50%, about 40% or about 30% of the amino acid sequence of the parent sortase. In some embodiments the fragment lacks an N-terminal portion of the parent sortase amino acid sequence that is not essential to the catalytic activity of sortase, for example the fragment lacks the N-terminal portion extending to the end of the membrane anchor sequence. In some embodiments the fragment comprises the C-terminus of a parent sortase amino acid sequence. In some embodiments, the fragment comprises the catalytic core region of a sortase. In one embodiment the core region is from about position 60 to about position 206 of *Staphylococcus aureus* Sortase A of SEQ ID NO: 01.

In the methods as reported herein the sortase, the sortase recognition sequence comprising polypeptide (i.e. the acyl donor), and the sortase acceptor sequence comprising polypeptide (i.e. the nucleophile/the acyl acceptor) are incubated together under conditions suitable to effect the formation of a peptide bond between the N-terminal part of the sortase recognition sequence comprising polypeptide and the C-terminal part of the sortase acceptor sequence comprising polypeptide. As used herein, the term "incubating" or grammatical equivalents thereof denotes that the listed components are brought in close proximity to one another to allow contact between the molecules. Incubating can be done by adding them to one reaction vessel, for example. The components in the system may be mixed in a variety of manners, such as by oscillating a vessel, subjecting a vessel to a vortex generating apparatus, or repeated mixing with a pipette or pipettes, for example. The components may be added in any order to the system.

The sortase reaction may be performed in any convenient vessel (e.g., tubes such as microfuge tubes, flask, dish), microtiter plates (e.g., 96-well or 384-well plates), glass slides, silicon chips, filters, or any solid or semisolid support having surface (optionally coated) having molecules immobilized thereon and optionally oriented in an array (see, e.g., U.S. Pat. No. 6,261,776 and Fodor, Nature 364 (1993) 555-556), and microfluidic devices (see, e.g., U.S. Pat. Nos. 6,440,722; 6,429,025; 6,379,974; and 6,316,781).

The reaction mixture is generally cell free and further does not include bacterial cell wall components or intact bacterial cell walls. In some embodiments, the sortase recognition sequence comprising polypeptide and/or the sortase acceptor sequence comprising polypeptide are expressed by one or more recombinant nucleotide sequences in a cell, which nucleotide sequences are integrated into the cell genome or are maintained non-integrated (e.g., in a plasmid).

The reaction mixture is maintained at any convenient temperature at which the sortase reaction can be performed. In some embodiments, the sortase reaction is performed at a temperature between and including about 15° C. and about 50° C. In one embodiment the incubating is at a temperature of from 30° C. to 40° C. In some embodiments, the sortase reaction is performed at a temperature between and including about 23° C. and about 37° C. In one embodiment the incubating is at a temperature of about 37° C. In certain embodiments, the temperature is room temperature (i.e. about 20° C. to 25° C.). The temperature can be optimized by repetitively performing the same sortase reaction at different temperatures and determining ligation rates.

Any convenient volume and component ratio can be used.

In certain embodiments, a (molar) ratio of 1:1000 or greater of sortase enzyme to sortase recognition sequence comprising polypeptide is utilized, or a (molar) ratio of 1:1000 or greater of sortase enzyme to sortase acceptor sequence comprising polypeptide is utilized. In specific embodiments, ratios of sortase enzyme to sortase recognition sequence comprising polypeptide or enzyme to sortase acceptor sequence comprising polypeptide is about 1:1, including 1:2 or greater, 1:3 or greater, 1:4 or greater, 1:5 or greater, 1:6 or greater, 1:7 or greater, 1:8 or greater, and 1:9 or greater.

In some embodiments, the sortase recognition sequence comprising polypeptide is present at a concentration ranging from about 10 µM to about 10 mM. In some embodiments, the sortase recognition sequence comprising polypeptide is present at a concentration ranging from about 100 µM to about 1 mM. In some embodiments, the sortase recognition sequence comprising polypeptide is present at a concentration ranging from about 100 µM to about 5 mM. In some embodiments, the sortase recognition sequence comprising polypeptide is present at a concentration ranging from about 200 µM to about 1 mM. In some embodiments, the sortase recognition sequence comprising polypeptide is present at a concentration ranging from about 200 µM to about 800 µM. In some embodiments, the sortase recognition sequence comprising polypeptide is present at a concentration ranging from about 400 µM to about 600 µM.

In certain embodiments, the sortase acceptor sequence comprising polypeptide is present at a concentration ranging from about 1 µM to about 500 µM. In certain embodiments, the sortase acceptor sequence comprising polypeptide is present at a concentration ranging from about 15 µM to about 150 µM. In certain embodiments, the sortase acceptor sequence comprising polypeptide is present at a concentration ranging from about 25 µM to about 100 µM. In certain embodiments, the sortase acceptor sequence comprising polypeptide is present at a concentration ranging from about 40 µM to about 60 µM.

In certain embodiments, the sortase is present at a concentration ranging from about 1 µM to about 500 µM. In certain embodiments, the sortase is present at a concentration ranging from about 15 µM to about 150 µM. In certain embodiments, the sortase is present at a concentration ranging from about 25 µM to about 100 µM. In certain embodiments, the sortase is present at a concentration ranging from about 40 µM to about 60 µM.

In certain embodiments, the method is performed in a reaction mixture comprising an aqueous environment. Water with an appropriate buffer and/or salt content often may be utilized. An alcohol or organic solvent may be included in certain embodiments. The amount of an organic solvent often does not appreciably esterify a protein or peptide in the ligation process (e.g., esterified protein or peptide often increase only by 5% or less upon addition of an alcohol or organic solvent). Alcohol and/or organic solvent contents sometimes are 20% or less, 15% or less, 10% or less or 5% or less, and in embodiments where a greater amount of an alcohol or organic solvent is utilized, 30% or less, 40% or less, 50% or less, 60% or less, 70% or less, or 80% or less alcohol or organic solvent is present. In certain embodiments, the reaction mixture includes only an alcohol or an organic solvent, with only limited amounts of water if it is present.

In some embodiments, the reaction mixture comprises a buffer. A person skilled in the art will be familiar with a variety of buffers that could be used in accordance with the methods as reported herein. In some embodiments, the buffer solution comprises calcium ions. In certain embodiments, the buffer solution does not contain substances that precipitate calcium ions. In some embodiments, the buffer solution does not include phosphate ions. In some embodiments, the buffer solution does not contain chelating agents.

In some embodiments, the method is performed at a pH value in the range of from 6 to 8.5. In some embodiments, the method is performed at a pH value in the range of from 6 to 8. In some embodiments, the method is performed at a pH value in the range of from 6 to 7.5. In some embodiments, the method is performed at a pH value in the range of from 6.5 to 8.5. In some embodiments, the method is performed at a pH value in the range of from 7 to 8.5. In some embodiments, the method is performed at a pH value in the range of from 7.5 to 8.5. In some embodiments, the method is performed at a pH value in the range of from 7.0 to 8.5. In some embodiments, the method is performed at a pH value in the range of from 7.3 to 7.8.

In some embodiments the reaction is performed in a deep eutectic solvent.

In one embodiment the deep eutectic solvent comprises choline chloride. In one embodiment the deep eutectic solvent is a mixture of choline chloride with glycerol at a molar ratio of 1:2. In one embodiment the deep eutectic solvent comprises an aqueous co-solvent. In one embodiment the deep eutectic solvent comprises up to 30% (v/v) co-solvent. In one embodiment the deep eutectic solvent comprises up to 15% (v/v) co-solvent. In one preferred embodiment the deep eutectic solvent is a mixture of choline chloride with glycerol at a molar ratio of 1:2 comprising up to 5% (v/v) aqueous co-solvent.

In one embodiment the deep eutectic solvent is a thiol-based deep eutectic solvent. In one embodiment the thiol-based deep eutectic solvent comprises a) at least one hydrogen bond acceptor, and b) at least one aliphatic hydrogen bond donor comprising i) at least one thiol group and ii) at least one hydroxy group or negatively charged oxygen atom or a salt thereof, wherein the molar ratio of the at least one hydrogen bond acceptor and the at least one aliphatic hydrogen bond donor is of from 2:1 to 1:10. In one embodiment the at least one hydrogen bond acceptor is choline chloride. In one embodiment the at least one hydrogen bond acceptor is selected from the group consisting of (2-hydroxyethyl) trimethyl ammonium salts, methyl triphenyl phosphonium salts, ethylene amine salts and tributyl amine salts. In one embodiment the salts are chlorides, bromines and hydroxides. In one embodiment the molar ratio of choline chloride and dithiothreitol is about 1:2.5 to 1:3. In one embodiment the molar ratio of choline chloride and 2-mercaptoethanol is about 1:2. In one embodiment the molar ratio of choline chloride and 4-mercapto-1-butanol is about 1:2. In one embodiment the molar ratio of choline chloride and 1-mercapto-2-propanol is about 1:2. In one preferred embodiment the molar ratio of choline chloride and sodium 2-mercaptoethansulfonate is about 1:1.

One or more components of the reaction mixture or the product may be immobilized to a solid support. The attachment between the reaction mixture component and the solid support may be covalent or non-covalent (see, e.g., U.S. Pat. No. 6,022,688 for non-covalent attachments). The solid support may be one or more surfaces of the system, such as one or more surfaces in each well of a microtiter plate, a surface of a glass slide or silicon wafer, BIAcore chip, a surface of a particle, e.g., a bead (see e.g., Lam, Nature 354 (1991) 82-84) that is optionally linked to another solid support, or a channel in a microfluidic device, for example. Types of solid supports, linker molecules for covalent and non-covalent attachments to solid supports, and methods for immobilizing molecules to solid supports are known (see, e.g., U.S. Pat. Nos. 6,261,776; 5,900,481; 6,133,436; 6,022, 688; WO 2001/18234). Any material may be used, e.g., plastic (e.g., polystyrene), metal, glass, cellulose, gels (e.g., formed at least in part from organic polymers such as PDMS), etc. In some embodiments the solid support is semi-solid and/or gel-like, deformable, flexible, or the like.

Any polypeptide, eventually after introduction of a sortase recognition sequence or an oligoglycine, may be used as sortase-motif comprising polypeptide or sortase acceptor sequence comprising polypeptide in the methods as reported herein.

Non-Sortase Motif Moiety

The sortase recognition sequence LPXTG (SEQ ID NO: 21) may be conjugated, if it is not directly comprised within the amino acid sequence of the polypeptide, to a therapeutic agent (drug), a toxic agent (e.g. a toxin such as doxorubicin or pertussis toxin), a fluorophore (e.g. a fluorescent dye like fluorescein or rhodamine), a chelating agent for an imaging or radiotherapeutic metal, a peptidyl or non-peptidyl label, a tag, or a clearance-modifying agent such as various isomers of polyethylene glycol, a peptide that binds to a third component, or another carbohydrate or lipophilic agent, or member of a binding pair (e.g. biotin). The conjugation can be either directly or via an intervening linker.

a) Therapeutic Agents

The drug moiety can be any compound, moiety or group which has a therapeutic effect, such as an antibody, a cytotoxic or cytostatic compound.

A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (a4-subunit of $\alpha 4\beta 1$ and $\alpha 4\beta 7$ integrins), ReoPro/Abciximab (gpIIb-gpIIa and $\alpha v\beta 3$-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAM5/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin(SGN-35)/Brentuximab (CD30), and ARH460-16-2 (CD44).

The conjugates obtained with the method as reported herein can be used in the preparation of medicaments for the treatment of e.g. an oncologic disease, a cardiovascular disease, an infectious disease, an inflammatory disease, an autoimmune disease, a metabolic (e.g., endocrine) disease, or a neurological (e.g. neurodegenerative) disease. Exemplary non-limiting examples of these diseases are Alzheimer's disease, non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas (such as carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes), melanomas, sarcomas, gliomas, and skin cancers, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

A number of cell surface markers and their ligands are known. For example cancer cells have been reported to express at least one of the following cell surface markers and or ligands, including but not limited to, carbonic anhydrase IX, alpha-fetoprotein, alpha-actinin-4, A3 (antigen specific for A33 antibody), ART-4, B7, Ba-733, BAGE, BrE3-antigen, CA125, CAMEL, CAP-1, CASP-8/m, CCCL19, CCCL21, CD1, CD1a, CD2, CD3, CD4, CDS, CD8, CD1-1A, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1-alpha, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, GROB, HLA-DR, HM1.24, human chorionic gonadotropin (HCG) and its subunits, HER2/neu, HMGB-1, hypoxia inducible factor (HIF-1), HSP70-2M, HST-2 or 1a, IGF-1R, IFN-gamma, IFN-alpha, IFN-beta, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, P1GF, ILGF, ILGF-1R, IL-6, IL-25, RS5, RANTES, T101, SAGE, S100, survivin, survivin-2B, TAC, TAG-72, tenascin, TRAIL receptors, TNF-alpha, Tn-antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi, et al., Clin. Cancer Res. 12 (2006) 5023-5032; Parmiani, et al, J. Immunol. 178 (2007) 1975-1979; Novellino, et al., Cancer Immunol. Immunother. 54 (2005) 187-207).

Thus, antibodies recognizing specific cell surface receptors including their ligands can be used for specific and selective targeting and binding to a number/multitude of cell surface markers that are associated with a disease. A cell surface marker is a polypeptide located on the surface of a cell (e.g. a disease-related cell) that is e.g. associated with signaling event or ligand binding.

In one embodiment, for the treatment of cancer/tumors multi specific binding molecules/bispecific antibodies are produced that target tumor-associated antigens, such as those reported in Herberman, "Immunodiagnosis of Cancer", in Fleisher (ed.), "The Clinical Biochemistry of Cancer", page 347 (American Association of Clinical Chemists (1979)) and in U.S. Pat. Nos. 4,150,149; 4,361,544; and 4,444,744.

Reports on tumor associated antigens (TAAs) include Mizukami, et al., (Nature Med. 11 (2005) 992-997); Hatfield, et al., (Curr. Cancer Drug Targets 5 (2005) 229-248); Vallbohmer, et al., (J Clin. Oncol. 23 (2005) 3536-3544); and Ren, et al., (Ann. Surg. 242 (2005) 55-63), each incorporated herein by reference with respect to the TAAs identified.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD54, CD67, CD74, CD79a, CD80, CD126, CD138, CD154, CXCR4, B7, MUC1 or 1a, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DR5).

A number of bispecific antibodies are known directed against two different targets, such as BCMA/CD3, different antigens of the HER family in combination (EGFR, HER2, HER3), CD19/CD3, IL17RA/IL7R, IL-6/IL-23, IL-1-beta/IL-8, IL-6 or IL-6R/IL-21 or IL-21R, first specificity directed to a glycoepitope of an antigen selected from the group consisting of Lewis x-, Lewis b- and Lewis y-structures, Globo H-structures, KH1, Tn-antigen, TF-antigen and carbohydrate structures of Mucins, CD44, glycolipids and glycosphingolipids, such as Gg3, Gb3, GD3, GD2, Gb5, Gm1, Gm2, sialyltetraosylceramide and a second specificity directed to an ErbB receptor tyrosine kinase selected from the group consisting of EGFR, HER2, HER3 and HER4, GD2 in combination with a second antigen binding site is associated with an immunological cell chosen from the group consisting of T-lymphocytes NK cell, B-lymphocytes, dendritic cells, monocytes, macrophages, neutrophils, mesenchymal stem cells, neural stem cells, ANG2/VEGF, VEGF/PDGFR-beta, Vascular Endothelial Growth Factor (VEGF) acceptor 2/CD3, PSMA/CD3, EPCAM/CD3, combinations of an antigen is selected from a group consisting of VEGFR-1, VEGFR-2, VEGFR-3, FLT3, c-FMS/CSF1R, RET, c-Met, EGFR, Her2/neu, HER3, HER4, IGFR, PDGFR, c-KIT, BCR, integrin and MMPs with a water-soluble ligand is selected from the group consisting of VEGF, EGF, PlGF, PDGF, HGF, and angiopoietin, ERBB-3/C-MET, ERBB-2/C-MET, EGF receptor 1/CD3, EGFR/HER3, PSCA/CD3, C-MET/CD3, ENDOSIALIN/CD3, EPCAM/CD3, IGF-1R/CD3, FAPALPHA/CD3, EGFR/IGF-1R, IL 17A/F, EGF receptor 1/CD3, and CD19/CD16.

b) Toxic Agent

Toxic drug moieties include: (i) chemotherapeutic agents, which may function as microtubule inhibitors, mitosis inhibitors, topoisomerase inhibitors, or DNA intercalators; (ii) protein toxins, which may function enzymatically; and (iii) radioisotopes.

Exemplary toxic drug moieties include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al., Science, 238 (1987) 1098), abrin A chain, modeccin A chain, alpha-sarcin, *Aleurites fordii* proteins, dianthin proteins, *Phytolaca americana* proteins (PAPI, PAPII, and PAP-5), *Momordica charantia* inhibitor, curcin, crotin, *Sapaonaria officinalis* inhibitor, gelonin, mitogellin, restrictocin, phenomycin, enomycin, and the tricothecenes (WO 93/21232).

c) Chelating Agent Comprising Radioisotope

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope or other labels may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

d) Labels

The non-sortase motif moiety can be a label. Any label moiety which can be covalently attached to the sortase amino acid sequence can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, such as biotin.

Conjugates comprising a haptenylated label may be useful in diagnostic assays, e.g., for detecting expression of an antigen of interest in specific cells, tissues, or serum. For diagnostic applications, a bispecific antibody will be used wherein the first binding specificity binds to a target and the second binding specificity binds to a haptenylated label. The hapten will typically be labeled with a detectable moiety. Numerous labels are available which can be generally grouped into the following categories:

(a) Radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi. Radioisotope labeled conjugates are useful in receptor targeted imaging experiments. The antigen (hapten) can be labeled with ligand reagents that bind, chelate or otherwise complex a radioisotope metal using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the complex as reported herein (Wu et al, Nature Biotechnology 23(9) (2005) 1137-1146). Receptor target imaging with radionuclide labeled complexes can provide a marker of pathway activation by detection and quantification of progressive accumulation of complexes or corresponding therapeutic antibodies in tumor tissue (Albert et al (1998) Bioorg. Med. Chem. Lett. 8:1207-1210).

Metal-chelate complexes suitable as labels for imaging experiments (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-220).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to the antigen (hapten) using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

Detection labels such as fluorescent dyes and chemiluminescent dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling, especially with the following properties: (i) the labeled conjugate should produce a very high signal with low background so that small quantities of conjugate can be sensitively detected in both cell-free and cell-based assays; and (ii) the labeled conjugate should be photostable so that the fluorescent signal may be observed, monitored and recorded without significant photo bleaching. For applications involving cell surface binding of labeled conjugates to membranes or cell surfaces, especially live cells, the labels should (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al "Methods for the Preparation of Enzyme-Antibody Conjugates for use in Enzyme Immunoassay", in Methods in Enzym. (ed. by J. Langone & IT Van Vunakis), Academic Press, New York, 73 (1981) 147-166.

Examples of enzyme-substrate combinations (U.S. Pat. Nos. 4,275,149; 4,318,980) include, for example:
(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));
(ii) alkaline phosphatase (AP) with para-nitrophenyl phosphate as chromogenic substrate; and
(iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al, Nuclear Medicine and Biology, 37(3) (2010) 289-297; Chen et al, Bioconjugate Chem. 15 (2004) 41-49; US 2010/0111856 (v) bioluminescence; (vi) fluorescence; and (vii) ultrasound. Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 markers are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labeling methods are well known. See Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGruyter, Berlin and New York; and Wong (1991) Chemistry of Protein Conjugation and Cross-linking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

e) Binding Pairs

Indirect detection systems comprise, for example, that the detection reagent, e.g., the detection antibody is labeled with a first partner of a bioaffine binding pair. Examples of suitable binding pairs are hapten or antigen/antibody, biotin or biotin analogues such as aminobiotin, iminobiotin or desthiobiotin/avidin or Streptavidin, sugar/lectin, nucleic acid or nucleic acid analogue/complementary nucleic acid, and receptor/ligand, e.g., steroid hormone receptor/steroid hormone. Preferred first binding pair members comprise hapten, antigen and hormone. Especially preferred are haptens like digoxin and biotin and analogues thereof. The second partner of such binding pair, e.g. an antibody, Streptavidin, etc., usually is labeled to allow for direct detection, e.g., by the labels as mentioned above.

Linker

The term "linker" denotes a bifunctional or multifunctional moiety which can be used to conjugate (link) a first moiety with a second moiety. Linked conjugates can be conveniently prepared using a linker having two reactive functionalities.

In one embodiment, a linker has a reactive site which has an electrophilic group that is reactive to a nucleophilic group present in the sortase amino acid sequence. Useful electrophilic groups include, but are not limited to, another thiol, maleimide and haloacetamide groups (see e.g. conjugation method at page 766 of Klussman et al, Bioconjugate Chemistry 15(4) (2004) 765-773).

Examples of thiol-reaction functional groups include, but are not limited to, thiol, maleimide, alpha-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates.

The linker may comprise amino acid residues which link the sortase amino acid sequence to the non-sortase motif moiety. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or □□amino acids, such as e.g. β-alanine, or co-amino acids such as 4-amino-butyric acid.

In another embodiment, the linker has a reactive functional group which has a nucleophilic group that is reactive to an electrophilic group present in the sortase amino acid sequence. Useful electrophilic groups include, but are not limited to, aldehyde and ketone carbonyl groups. The heteroatom of a nucleophilic group of a linker can react with an electrophilic group in the sortase amino acid sequence and form a covalent bond to the sortase amino acid sequence. Useful nucleophilic groups on a linker include, but are not limited to, hydrazide, oxime, amino, hydrazine, thiosemicarbazone, hydrazine carboxylate, and arylhydrazide. The electrophilic group on an antigen (hapten) provides a convenient site for attachment to a linker.

Typically, peptide-type linkers can be prepared by forming a peptide bond between two or more amino acids and/or peptide fragments. Such peptide bonds can be prepared, for example, according to the liquid phase synthesis method (E. Schroder and K. Lubke "The Peptides", volume 1 (1965) 76-136, Academic Press) which is well known in the field of peptide chemistry.

In another embodiment, the linker may be substituted with groups which modulated solubility or reactivity. For example, a charged substituent such as sulfonate ($SO_3^-$) or ammonium or a polymer such as PEG, may increase water solubility of the reagent and facilitate the coupling reaction of the linker reagent with the antigen (hapten) or the drug moiety, or facilitate the coupling reaction depending on the synthetic route employed.

The conjugates comprising a non-sortase motif moiety as reported herein expressly contemplate, but are not limited to, complexes prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate), and including bis-maleimide reagents: DTME, BMB, BMDB, BMH, BMOE, BM(PEO)$_3$, and BM(PEO)$_4$, which are commercially available from Pierce Biotechnology, Inc. Bis-maleimide reagents allow the attachment of e.g. a thiol group to a thiol-containing drug moiety, label, or linker intermediate, in a sequential or concurrent fashion. Other functional groups besides maleimide, which are reactive with e.g. a thiol group, include iodoacetamide, bromoacetamide, vinyl pyridine, disulfide, pyridyl disulfide, isocyanate, and isothiocyanate.

Exemplary linker include a valine-citrulline (val-cit or vc) dipeptide linker reagent having a maleimide stretcher and a para-aminobenzylcarbamoyl (PAB) self-immolative spacer, and a phe-lys(Mtr) dipeptide linker reagent having a maleimide Stretcher unit and a p-amino benzyl self-immolative spacer.

Cysteine thiol groups are nucleophilic and capable of reacting to form covalent bonds with electrophilic groups on linker reagents and the non-sortase motif moiety or the sortase amino acid sequence including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a haptenylated compound include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

IV. RECOMBINANT METHODS

Any polypeptide, such as e.g. a mutated sortase as reported herein as well as a single chain antigen binding polypeptide such as a scFv, a scFab, or a darpin, or a multi chain antigen binding polypeptide such as a dsFv or a Fab comprising an sortase recognition sequence or a sortase acceptor sequence can be expressed and purified from the supernatant of eukaryotic cells (e.g. HEK293 cells, CHO cells). It does not matter if the polypeptide is an isolated polypeptide or comprised in a multimeric or heteromeric entity.

Suitable host cells for cloning or expression/secretion of polypeptide-encoding vectors include prokaryotic or eukaryotic cells described herein. For example, polypeptides may be produced in bacteria, in particular when glycosylation is not needed (see, e.g., U.S. Pat. Nos. 5,648,237, 5,789,199 and 5,840,523, Charlton, Methods in Molecular Biology 248 (2003) 245-254 (B.K.C. Lo, (ed.), Humana Press, Totowa, N.J.), describing expression of antibody fragments in *E. coli*). After expression, the polypeptide may be isolated from the bacterial cell paste in a soluble fraction or may be isolated from the insoluble fraction so called inclusion bodies which can be solubilized and refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978 and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are the COS-7 cell line (monkey kidney CV1 cell transformed by SV40); the HEK293 cell line (human embryonic kidney); the BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line (e.g. described in Mather, et al., Anal. N.Y. Acad. Sci. 383 (1982) 44-68); the MRC5 cell line; and the FS4 cells-line. Other useful mammalian host cell lines include the CHO cell line (Chinese hamster ovary cell), including DHFR negative CHO cell lines (see e.g. Urlaub, et al., Proc. Natl. Acad. Sci. USA 77 (1980) 4216), and myeloma cell lines such as Y0, NS0 and Sp2/0 cell line. For a review of certain mammalian host cell lines suitable for polypeptide production, see, e.g., Yazaki, and Wu, Methods in Molecular Biology, Antibody Engineering 248 (2004) 255-268 (B.K.C. Lo, (ed.), Humana Press, Totowa, N.J.).

The following examples and sequences are provided to aid the understanding of the present invention, the true scope of which is set forth in the appended claims. It is understood

V. EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements is used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a gene/protein to be expressed (e.g. full length antibody heavy chain), and
- the bovine growth hormone polyadenylation sequence (BGH pA).

Beside the expression unit/cassette including the desired gene to be expressed the basic/standard mammalian expression plasmid contains
- an origin of replication from the vector pUC18 which allows replication of this plasmid in *E. coli*, and
- a beta-lactamase gene which confers ampicillin resistance in *E. coli*.

Protein Determination

The protein concentration of purified polypeptides was determined by determining the optical density (OD) at 280 nm, using the molar extinction coefficient calculated on the basis of the amino acid sequence of the polypeptide.

Example 1

Generation of an Expression Plasmid for Sortases

The expression plasmid for the transient expression of soluble sortase in HEK293 cells comprised besides the soluble sortase expression cassette an origin of replication from the vector pUC18, which allows replication of this plasmid in *E. coli*, and a beta-lactamase gene which confers ampicillin resistance in *E. coli*.

The transcription unit of the soluble sortase comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a purification tag encoding nucleic acid,
- a sortase encoding nucleic acid, and
- the bovine growth hormone polyadenylation sequence (BGH pA).

The amino acid sequence of the mature wild-type soluble sortase is

```
                                        (SEQ ID NO: 11)
QAKPQIPKDKSKVAGYIEIPDADIKEPVYPGPATPEQLNRGVSFAEEN

ESLDDQNISIAGHTFIDRPNYQFTNLKAAKKGSMVYFKVGNETRKYKM

TSIRDVKPTDVGVLDEQKGKDKQLTLITCDDYNEKTGVWEKRKIFVAT

EVK.
```

The amino acid sequence of the mutated sortases as reported herein is

```
Q

AKPQIPKDKS KVAGYIEIPD ADIKEPVYPG PATPEQLNRG

VSFAEENESL DDQNISIAGH TFIDRPNYQF TNLKAAKKGS

MVYFKVGNET RKYKMTSIRD VKPTDVGVLD EQKGKDKQLT

LITCDDYNEK TGVWEKRKIF VATEVK
``` wherein the underlined residues are mutated to serine. Optionally one of the bold residues can also be mutated.

The purification tag has the amino acid sequence MRGSHHHHHHGS (SEQ ID NO: 51).

Example 2

Transient Expression and Analytical Characterization

The recombinant production was performed by transient transfection of HEK293 cells (human embryonic kidney cell line 293-derived) cultivated in F17 Medium (Invitrogen Corp.). For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).

General information regarding the recombinant expression of human immunoglobulins in e.g. HEK293 cells is given in: Meissner, P. et al., Biotechnol. Bioeng. 75 (2001) 197-203.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

Example 3

Library Construction and Expression

Simultaneous multiple site saturation (OminiChange) was done as described by Dennig, A., et al. (PLoS ONE 6 (2011) e26222). EpPCR (sequence saturation mutagenesis, SeSam) was done as describe by Wong, T. S., et al. (Nucl. Acids Res. 32 (2004) e26). Single site saturation was done using primers with NNK at the position which should be mutated. The mutated sortases were expressed using an expression system in 4× yeast media. Therefore, 200 µl were inoculated and incubated overnight at 37° C. Of this culture 20 µl were used to inoculate 200 µl 4× yeast media containing IPTG to induce the sortase expression. After 7 h at 37° C. the culture was mixed with glycerin to a final concentration of 12.5% and stored at −20° C.

Example 4

Library Screening with a Sortase Activity Assay

With the method as outlined below the activity of a sortase-mediated enzymatic conjugation/coupling reaction can be determined photometrically by fusing a glucose dehydrogenase as reporter enzyme to a sortase amino acid motif (LPETG (SEQ ID NO: 22)) and using this as first substrate. As second substrate biotinylated oligo-glycine or oligo-alanine is used (nucleophile). When the sortase is added to a solution containing the first and the second substrate a conjugate is formed by sortase-mediated conjugation of the first and the second substrate which is a biotinylated reporter enzyme. The biotinylated reporter enzyme can be recovered using a streptavidin-coated multi titer plate. When a substrate for the reporter enzyme is added, the product can be detected by the change of optical density.

Purified sortase was mixed with its substrates, i.e. a glucose dehydrogenase containing the LPETG motif (20 µM) and a biotin derivative containing N-terminal glycines (20 µM) in 50 mM Tris buffer pH 7.5 containing 200 mM NaCl. The reaction mixture was incubated at 37° C. for two hours. The reaction was stopped by addition of a 10- to 40-fold excess of inhibition buffer (50 mM Tris, pH 7.5, 200 mM NaCl, 10 mM CaCl2, 5 mM iodoacetamide). The stopped reaction mixture was centrifuged for 10 min. at 5000×g. The supernatant (50 µL) was added to 100 µL of 50 mM Tris buffer (pH 7.5) comprising 200 mM NaCl, 10 mM CaCl2 and added on a streptavidin coted multi titer plate and incubated for 30 min. at 30° C. at 200 rpm. Thereafter the multi titer plate was washed five times with 300 µL washing buffer each (50 mM Tris, pH 7.5, 200 mM NaCl, 10 mM CaCl2, 5 mg/mL BSA, 0.1% Triton X-100). Thereto 150 µL test buffer (0.2 M sodium citrate, pH 5.8, 0.3 g/L 4-nitrosoanilin, 1 mM CaCl2, 30 mM glucose) was added.

The kinetic of the reporter enzyme is measured over a time period of 5 min. at 620 nm. The activity of the reporter enzyme is proportional to the amount of immobilized enzyme, which is proportional to the amount of biotinylated enzyme and this is proportional to the activity of the sortase.

Example 5

Km Value Estimation (Activity at Low Substrate Concentrations)

Estimation of the Km Value of the Sortase Mutants.

The activity of the mutant in the lysate was determined with high and low substrate concentration. The quotient (activity low substrate concentration/activity high substrate concentration was calculated and compared with the parent of the mutants. A higher quotient represents a mutant with a lower Km.

For LPKTG: Low: 4 µM, High: 20 µM
For GGGG: Low 0.5 µM, High 20 µM

Example 6

Sortase Variant Stability Determination

Estimation of the Stability of the Screened Mutants.

The activity of the mutant in the lysate was determined without and with pre-heat-treatment (30 min, 60-65° C.). The quotient (activity after heat-treatment/activity bevor heat-treatment) was calculated and compered with the parent of the mutants. A higher quotient represents a mutant with a higher stability.

What is claimed is:

1. A method for improving enzymatic activity of a sortase comprising providing a sortase comprising an amino acid sequence that is at least 90% identical to the amino acid sequence of SEQ ID NO: 11, and mutating residues D101 and K137 to D101S and K137S, respectively, wherein said amino acid positions are based on the amino acid sequence of SEQ ID NO: 11, thereby obtaining a sortase with improved enzymatic activity as compared to a sortase comprising the amino acid sequence of SEQ ID NO: 11.

2. The method of claim 1, wherein the improved enzymatic is at least one selected from the group consisting of:
   (a) increased speed in catalyzing a transpeptidation reaction compared to a sortase having the amino acid sequence of SEQ ID NO: 11;
   (b) higher turnover rate in catalyzing a transpeptidation reaction compared to a sortase having the amino acid sequence of SEQ ID NO: 11;
   (c) increased or decreased affinity to a substrate compared to a sortase having the amino acid sequence of SEQ ID NO: 11; and
   (d) increased enzymatic activity in catalyzing a sortase mediated coupling reaction compared to a sortase having the amino acid sequence of SEQ ID NO: 11.

3. The method of claim 1, wherein the sortase with improved enzymatic activity further comprises one or more mutations selected from the group consisting of mutations at the amino acid positions A2, E47, N48, F85, and G108 to A2E/T, E47G, N48W, F85L, and G108E, wherein said amino acid positions are based on the amino acid sequence of SEQ ID NO: 11.

4. The method of claim 1, wherein the sortase with improved enzymatic activity comprises one or more sets of mutations selected from the group consisting of:
   (a) D101S, K137S, and E47G;
   (b) D101S, K137S, and N48W;
   (c) D101S, K137S, and F85L;
   (d) D101S, K137S, and G108E;
   (e) D101S, K137S, N48W, and F85L;
   (f) D101S, K137S, F85L, and G108E;
   (g) D101S, K137S, N48W, and G108E; and
   (h) D101S, K137S, N48W, F85L, and G108E.

5. The method of claim 1, wherein the sortase with improved enzymatic activity comprises an amino acid sequence selected from the group consisting of SEQ ID NO: 02, SEQ ID NO: 03, SEQ ID NO: 04, SEQ ID NO: 05, SEQ ID NO: 06, SEQ ID NO: 07, SEQ ID NO: 08, SEQ ID NO: 09, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

* * * * *

SEQUENCE LISTING

```
<160> NUMBER OF SEQ ID NOS: 52

<210> SEQ ID NO 1
<211> LENGTH: 206
<212> TYPE: PRT
<213> ORGANISM: Staphylococcus aureus

<400> SEQUENCE: 1

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125
```

```
Gln Phe Thr Asn Leu Lys Ala Ala Lys Lys Gly Ser Met Val Tyr Phe
        130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
        180                 185                 190

Val Trp Glu Lys Arg Lys Ile Phe Val Ala Thr Glu Val Lys
        195                 200                 205

<210> SEQ ID NO 2
<211> LENGTH: 206
<212> TYPE: PRT
<213> ORGANISM: Artificial Sequence
<220> FEATURE:
<223> OTHER INFORMATION: Staph. aureus Sortase A D160S-K196S

<400> SEQUENCE: 2

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
                20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Gln Ala Lys Pro Gln
50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
        100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
        130                 135                 140

Lys Val Gly Asn Glu Thr Arg Lys Tyr Lys Met Thr Ser Ile Arg Ser
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
        180                 185                 190

Val Trp Glu Ser Arg Lys Ile Phe Val Ala Thr Glu Val Lys
        195                 200                 205

<210> SEQ ID NO 3
<211> LENGTH: 206
<212> TYPE: PRT
<213> ORGANISM: Artificial Sequence
<220> FEATURE:
<223> OTHER INFORMATION: Staph. aureus Sortase A D160S-K196S-E106G

<400> SEQUENCE: 3

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
```

```
            20                  25                  30

Leu His Asp Lys Asp Lys Asp Glu Lys Ile Glu Gln Tyr Asp Lys Asn
            35                  40                  45

Val Lys Glu Gln Ala Ser Lys Asp Lys Gln Gln Ala Lys Pro Gln
        50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Gly Asn Glu Ser Leu Asp Asp
            100                 105                 110

Gln Asn Ile Ser Ile Ala Gly His Thr Phe Ile Asp Arg Pro Asn Tyr
            115                 120                 125

Gln Phe Thr Asn Leu Lys Ala Ala Lys Lys Gly Ser Met Val Tyr Phe
            130                 135                 140

Lys Val Gly Asn Glu Thr Arg Lys Tyr Lys Met Thr Ser Ile Arg Ser
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Ser Arg Lys Ile Phe Val Ala Thr Glu Val Lys
            195                 200                 205

<210> SEQ ID NO 4
<211> LENGTH: 206
<212> TYPE: PRT
<213> ORGANISM: Artificial Sequence
<220> FEATURE:
<223> OTHER INFORMATION: Staph. aureus Sortase A D160S-K196S-N107W

<400> SEQUENCE: 4

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
            35                  40                  45

Val Lys Glu Gln Ala Ser Lys Asp Lys Gln Gln Ala Lys Pro Gln
        50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Trp Glu Ser Leu Asp Asp
            100                 105                 110

Gln Asn Ile Ser Ile Ala Gly His Thr Phe Ile Asp Arg Pro Asn Tyr
            115                 120                 125

Gln Phe Thr Asn Leu Lys Ala Ala Lys Lys Gly Ser Met Val Tyr Phe
            130                 135                 140

Lys Val Gly Asn Glu Thr Arg Lys Tyr Lys Met Thr Ser Ile Arg Ser
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
```

```
                180                 185                 190
Val Trp Glu Ser Arg Lys Ile Phe Val Ala Thr Glu Val Lys
        195                 200                 205

<210> SEQ ID NO 5
<211> LENGTH: 206
<212> TYPE: PRT
<213> ORGANISM: Artificial Sequence
<220> FEATURE:
<223> OTHER INFORMATION: Staph. aureus Sortase A D160S-K196S-F144L

<400> SEQUENCE: 5

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Leu
    130                 135                 140

Lys Val Gly Asn Glu Thr Arg Lys Tyr Lys Met Thr Ser Ile Arg Ser
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Ser Arg Lys Ile Phe Val Ala Thr Glu Val Lys
        195                 200                 205

<210> SEQ ID NO 6
<211> LENGTH: 206
<212> TYPE: PRT
<213> ORGANISM: Artificial Sequence
<220> FEATURE:
<223> OTHER INFORMATION: Staph. aureus Sortase A D160S-K196S-G167E

<400> SEQUENCE: 6

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80
```

```
Ala Asp Ile Lys Glu Pro Val Tyr Pro Gly Pro Ala Thr Pro Glu Gln
                 85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
            115                 120                 125

Gln Phe Thr Asn Leu Lys Ala Ala Lys Lys Gly Ser Met Val Tyr Phe
        130                 135                 140

Lys Val Gly Asn Glu Thr Arg Lys Tyr Lys Met Thr Ser Ile Arg Ser
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
                180                 185                 190

Val Trp Glu Ser Arg Lys Ile Phe Val Ala Thr Glu Val Lys
                195                 200                 205
```

<210> SEQ ID NO 7
<211> LENGTH: 206
<212> TYPE: PRT
<213> ORGANISM: Artificial Sequence
<220> FEATURE:
<223> OTHER INFORMATION: Staph. aureus Sortase A D160S-K196S-N107W-F144L

<400> SEQUENCE: 7

```
Met Lys Lys Trp Thr Asn Arg Leu Met Thr Ile Ala Gly Val Val Leu
1               5                  10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Ala Lys Pro Gln
 50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                 85                  90                  95

Leu Asn Arg Gly Val Ser Phe Ala Glu Glu Trp Glu Ser Leu Asp Asp
            100                 105                 110

Gln Asn Ile Ser Ile Ala Gly His Thr Phe Ile Asp Arg Pro Asn Tyr
            115                 120                 125

Gln Phe Thr Asn Leu Lys Ala Ala Lys Lys Gly Ser Met Val Tyr Leu
        130                 135                 140

Lys Val Gly Asn Glu Thr Arg Lys Tyr Lys Met Thr Ser Ile Arg Ser
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
                180                 185                 190

Val Trp Glu Ser Arg Lys Ile Phe Val Ala Thr Glu Val Lys
                195                 200                 205
```

<210> SEQ ID NO 8
<211> LENGTH: 206
<212> TYPE: PRT
<213> ORGANISM: Artificial Sequence
<220> FEATURE:

<223> OTHER INFORMATION: Staph. aureus Sortase A D160S-K196S-F144L-G167E

<400> SEQUENCE: 8

| Met | Lys | Lys | Trp | Thr | Asn | Arg | Leu | Met | Thr | Ile | Ala | Gly | Val | Val | Leu |
|---|---|---|---|---|---|---|---|---|---|---|---|---|---|---|---|
| 1 | | | | 5 | | | | | 10 | | | | | 15 | |

Ile Leu Val Ala Ala Tyr Leu Phe Ala Lys Pro His Ile Asp Asn Tyr
              20                  25                  30

Leu His Asp Lys Asp Lys Asp Glu Lys Ile Glu Gln Tyr Asp Lys Asn
          35                  40                  45

Val Lys Glu Gln Ala Ser Lys Asp Lys Gln Gln Ala Lys Pro Gln
 50                  55                  60

Ile Pro Lys Asp Lys Ser Lys Val Ala Gly Tyr Ile Glu Ile Pro Asp
 65                  70                  75                  80

Ala Asp Ile Lys Glu Pro Val Tyr Pro Gly Pro Ala Thr Pro Glu Gln
              85                  90                  95

Leu Asn Arg Gly Val Ser Phe Ala Glu Glu Asn Glu Ser Leu Asp Asp
              100                 105                 110

Gln Asn Ile Ser Ile Ala Gly His Thr Phe Ile Asp Arg Pro Asn Tyr
              115                 120                 125

Gln Phe Thr Asn Leu Lys Ala Ala Lys Lys Gly Ser Met Val Tyr Leu
 130                 135                 140

Lys Val Gly Asn Glu Thr Arg Lys Tyr Lys Met Thr Ser Ile Arg Ser
145                 150                 155                 160

Val Lys Pro Thr Asp Val Glu Val Leu Asp Glu Gln Lys Gly Lys Asp
              165                 170                 175

Lys Gln Leu Thr Leu Ile Thr Cys Asp Asp Tyr Asn Glu Lys Thr Gly
              180                 185                 190

Val Trp Glu Ser Arg Lys Ile Phe Val Ala Thr Glu Val Lys
              195                 200                 205

<210> SEQ ID NO 9
<211> LENGTH: 206
<212> TYPE: PRT
<213> ORGANISM: Artificial Sequence
<220> FEATURE:
<223> OTHER INFORMATION: Staph. aureus Sortase A D160S-K196S-N107W-G167E

<400> SEQUENCE: 9

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
              20                  25                  30

Leu His Asp Lys Asp Lys Asp Glu Lys Ile Glu Gln Tyr Asp Lys Asn
          35                  40                  45

Val Lys Glu Gln Ala Ser Lys Asp Lys Gln Gln Ala Lys Pro Gln
 50                  55                  60

Ile Pro Lys Asp Lys Ser Lys Val Ala Gly Tyr Ile Glu Ile Pro Asp
 65                  70                  75                  80

Ala Asp Ile Lys Glu Pro Val Tyr Pro Gly Pro Ala Thr Pro Glu Gln
              85                  90                  95

Leu Asn Arg Gly Val Ser Phe Ala Glu Glu Trp Glu Ser Leu Asp Asp
              100                 105                 110

Gln Asn Ile Ser Ile Ala Gly His Thr Phe Ile Asp Arg Pro Asn Tyr
              115                 120                 125

Gln Phe Thr Asn Leu Lys Ala Ala Lys Lys Gly Ser Met Val Tyr Phe
 130                 135                 140

```
Lys Val Gly Asn Glu Thr Arg Lys Tyr Lys Met Thr Ser Ile Arg Ser
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Ser Arg Lys Ile Phe Val Ala Thr Glu Val Lys
        195                 200                 205

<210> SEQ ID NO 10
<211> LENGTH: 206
<212> TYPE: PRT
<213> ORGANISM: Artificial Sequence
<220> FEATURE:
<223> OTHER INFORMATION: Staph. aureus Sortase A
      D160S-K196S-N107W-F144-L-G167E

<400> SEQUENCE: 10

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Trp Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Leu
    130                 135                 140

Lys Val Gly Asn Glu Thr Arg Lys Tyr Lys Met Thr Ser Ile Arg Ser
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Ser Arg Lys Ile Phe Val Ala Thr Glu Val Lys
        195                 200                 205

<210> SEQ ID NO 11
<211> LENGTH: 147
<212> TYPE: PRT
<213> ORGANISM: Artificial Sequence
<220> FEATURE:
<223> OTHER INFORMATION: shortened Staph. aureus Sortase A

<400> SEQUENCE: 11

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30
```

```
Ala Thr Pro Glu Gln Leu Asn Arg Gly Val Ser Phe Ala Glu Glu Asn
            35                  40                  45

Glu Ser Leu Asp Asp Gln Asn Ile Ser Ile Ala Gly His Thr Phe Ile
 50                      55                  60

Asp Arg Pro Asn Tyr Gln Phe Thr Asn Leu Lys Ala Ala Lys Lys Gly
 65                  70                  75                  80

Ser Met Val Tyr Phe Lys Val Gly Asn Glu Thr Arg Lys Tyr Lys Met
                 85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
            115                 120                 125

Asn Glu Lys Thr Gly Val Trp Glu Lys Arg Lys Ile Phe Val Ala Thr
130                 135                 140

Glu Val Lys
145

<210> SEQ ID NO 12
<211> LENGTH: 147
<212> TYPE: PRT
<213> ORGANISM: Artificial Sequence
<220> FEATURE:
<223> OTHER INFORMATION: shortened Staph. aureus Sortase A D101S-K137S

<400> SEQUENCE: 12

Gln Ala Lys Pro Gln Ile Pro Lys Asp Lys Ser Lys Val Ala Gly Tyr
 1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Asn
            35                  40                  45

Glu Ser Leu Asp Asp Gln Asn Ile Ser Ile Ala Gly His Thr Phe Ile
 50                      55                  60

Asp Arg Pro Asn Tyr Gln Phe Thr Asn Leu Lys Ala Ala Lys Lys Gly
 65                  70                  75                  80

Ser Met Val Tyr Phe Lys Val Gly Asn Glu Thr Arg Lys Tyr Lys Met
                 85                  90                  95

Thr Ser Ile Arg Ser Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
            115                 120                 125

Asn Glu Lys Thr Gly Val Trp Glu Ser Arg Lys Ile Phe Val Ala Thr
130                 135                 140

Glu Val Lys
145

<210> SEQ ID NO 13
<211> LENGTH: 147
<212> TYPE: PRT
<213> ORGANISM: Artificial Sequence
<220> FEATURE:
<223> OTHER INFORMATION: shortened Staph. aureus Sortase A
      D101S-K137S-E47G

<400> SEQUENCE: 13

Gln Ala Lys Pro Gln Ile Pro Lys Asp Lys Ser Lys Val Ala Gly Tyr
 1               5                   10                  15

Ile Glu Ile Pro Asp Ala Asp Ile Lys Glu Pro Val Tyr Pro Gly Pro
```

```
                    20                  25                  30
Ala Thr Pro Glu Gln Leu Asn Arg Gly Val Ser Phe Ala Glu Gly Asn
                35                  40                  45

Glu Ser Leu Asp Asp Gln Asn Ile Ser Ile Ala Gly His Thr Phe Ile
        50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Ser Val Lys Pro Thr Asp Val Gly Val Leu Asp Glu
                100                 105                 110

Gln Lys Gly Lys Asp Lys Gln Leu Thr Leu Ile Thr Cys Asp Asp Tyr
            115                 120                 125

Asn Glu Lys Thr Gly Val Trp Glu Ser Arg Lys Ile Phe Val Ala Thr
        130                 135                 140

Glu Val Lys
145

<210> SEQ ID NO 14
<211> LENGTH: 147
<212> TYPE: PRT
<213> ORGANISM: Artificial Sequence
<220> FEATURE:
<223> OTHER INFORMATION: shortened Staph. aureus Sortase A
      D101S-K137S-N48W

<400> SEQUENCE: 14

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
                20                  25                  30

Ala Thr Pro Glu Gln Leu Asn Arg Gly Val Ser Phe Ala Glu Glu Trp
                35                  40                  45

Glu Ser Leu Asp Asp Gln Asn Ile Ser Ile Ala Gly His Thr Phe Ile
        50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Ser Val Lys Pro Thr Asp Val Gly Val Leu Asp Glu
                100                 105                 110

Gln Lys Gly Lys Asp Lys Gln Leu Thr Leu Ile Thr Cys Asp Asp Tyr
            115                 120                 125

Asn Glu Lys Thr Gly Val Trp Glu Ser Arg Lys Ile Phe Val Ala Thr
        130                 135                 140

Glu Val Lys
145

<210> SEQ ID NO 15
<211> LENGTH: 147
<212> TYPE: PRT
<213> ORGANISM: Artificial Sequence
<220> FEATURE:
<223> OTHER INFORMATION: shortened Staph. aureus Sortase A
      D101S-K137S-F85L

<400> SEQUENCE: 15

Gln Ala Lys Pro Gln Ile Pro Lys Asp Lys Ser Lys Val Ala Gly Tyr
```

-continued

```
                1               5                   10                  15
              Ile Glu Ile Pro Asp Ala Asp Ile Lys Glu Pro Val Tyr Pro Gly Pro
                                20                  25                  30
              Ala Thr Pro Glu Gln Leu Asn Arg Gly Val Ser Phe Ala Glu Glu Asn
                                35                  40                  45
              Glu Ser Leu Asp Asp Gln Asn Ile Ser Ile Ala Gly His Thr Phe Ile
                                50                  55                  60
              Asp Arg Pro Asn Tyr Gln Phe Thr Asn Leu Lys Ala Ala Lys Lys Gly
              65                  70                  75                  80
              Ser Met Val Tyr Leu Lys Val Gly Asn Glu Thr Arg Lys Tyr Lys Met
                                85                  90                  95
              Thr Ser Ile Arg Ser Val Lys Pro Thr Asp Val Gly Val Leu Asp Glu
                                100                 105                 110
              Gln Lys Gly Lys Asp Lys Gln Leu Thr Leu Ile Thr Cys Asp Asp Tyr
                                115                 120                 125
              Asn Glu Lys Thr Gly Val Trp Glu Ser Arg Lys Ile Phe Val Ala Thr
                                130                 135                 140
              Glu Val Lys
              145

<210> SEQ ID NO 16
<211> LENGTH: 147
<212> TYPE: PRT
<213> ORGANISM: Artificial Sequence
<220> FEATURE:
<223> OTHER INFORMATION: shortened Staph. aureus Sortase A
      D101S-K137S-G108E

<400> SEQUENCE: 16

Gln Ala Lys Pro Gln Ile Pro Lys Asp Lys Ser Lys Val Ala Gly Tyr
              1               5                   10                  15
              Ile Glu Ile Pro Asp Ala Asp Ile Lys Glu Pro Val Tyr Pro Gly Pro
                                20                  25                  30
              Ala Thr Pro Glu Gln Leu Asn Arg Gly Val Ser Phe Ala Glu Glu Asn
                                35                  40                  45
              Glu Ser Leu Asp Asp Gln Asn Ile Ser Ile Ala Gly His Thr Phe Ile
                                50                  55                  60
              Asp Arg Pro Asn Tyr Gln Phe Thr Asn Leu Lys Ala Ala Lys Lys Gly
              65                  70                  75                  80
              Ser Met Val Tyr Phe Lys Val Gly Asn Glu Thr Arg Lys Tyr Lys Met
                                85                  90                  95
              Thr Ser Ile Arg Ser Val Lys Pro Thr Asp Val Glu Val Leu Asp Glu
                                100                 105                 110
              Gln Lys Gly Lys Asp Lys Gln Leu Thr Leu Ile Thr Cys Asp Asp Tyr
                                115                 120                 125
              Asn Glu Lys Thr Gly Val Trp Glu Ser Arg Lys Ile Phe Val Ala Thr
                                130                 135                 140
              Glu Val Lys
              145

<210> SEQ ID NO 17
<211> LENGTH: 147
<212> TYPE: PRT
<213> ORGANISM: Artificial Sequence
<220> FEATURE:
<223> OTHER INFORMATION: shortened Staph. aureus Sortase A
      D101S-K137S-N48W-F85L
```

<400> SEQUENCE: 17

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
                20                  25                  30

Ala Thr Pro Glu Gln Leu Asn Arg Gly Val Ser Phe Ala Glu Glu Trp
            35                  40                  45

Glu Ser Leu Asp Asp Gln Asn Ile Ser Ile Ala Gly His Thr Phe Ile
    50                  55                  60

Asp Arg Pro Asn Tyr Gln Phe Thr Asn Leu Lys Ala Ala Lys Lys Gly
65                  70                  75                  80

Ser Met Val Tyr Leu Lys Val Gly Asn Glu Thr Arg Lys Tyr Lys Met
                85                  90                  95

Thr Ser Ile Arg Ser Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Ser Arg Lys Ile Phe Val Ala Thr
    130                 135                 140

Glu Val Lys
145

<210> SEQ ID NO 18
<211> LENGTH: 147
<212> TYPE: PRT
<213> ORGANISM: Artificial Sequence
<220> FEATURE:
<223> OTHER INFORMATION: shortened Staph. aureus Sortase A
      D101S-K137S-F85L-G108E

<400> SEQUENCE: 18

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
                20                  25                  30

Ala Thr Pro Glu Gln Leu Asn Arg Gly Val Ser Phe Ala Glu Glu Asn
            35                  40                  45

Glu Ser Leu Asp Asp Gln Asn Ile Ser Ile Ala Gly His Thr Phe Ile
    50                  55                  60

Asp Arg Pro Asn Tyr Gln Phe Thr Asn Leu Lys Ala Ala Lys Lys Gly
65                  70                  75                  80

Ser Met Val Tyr Leu Lys Val Gly Asn Glu Thr Arg Lys Tyr Lys Met
                85                  90                  95

Thr Ser Ile Arg Ser Val Lys Pro Thr Asp Val Glu Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Ser Arg Lys Ile Phe Val Ala Thr
    130                 135                 140

Glu Val Lys
145

<210> SEQ ID NO 19
<211> LENGTH: 147
<212> TYPE: PRT
<213> ORGANISM: Artificial Sequence
<220> FEATURE:

-continued

<223> OTHER INFORMATION: shortened Staph. aureus Sortase A
D101S-K137S-N48W-G108E

<400> SEQUENCE: 19

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Trp
        35                  40                  45

Glu Ser Leu Asp Asp Gln Asn Ile Ser Ile Ala Gly His Thr Phe Ile
50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Ser Val Lys Pro Thr Asp Val Glu Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Ser Arg Lys Ile Phe Val Ala Thr
130                 135                 140

Glu Val Lys
145

<210> SEQ ID NO 20
<211> LENGTH: 147
<212> TYPE: PRT
<213> ORGANISM: Artificial Sequence
<220> FEATURE:
<223> OTHER INFORMATION: shortened Staph. aureus Sortase A
D101S-K137S-N48W-F85L-G108E

<400> SEQUENCE: 20

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Trp
        35                  40                  45

Glu Ser Leu Asp Asp Gln Asn Ile Ser Ile Ala Gly His Thr Phe Ile
50                  55                  60

Asp Arg Pro Asn Tyr Gln Phe Thr Asn Leu Lys Ala Ala Lys Lys Gly
65                  70                  75                  80

Ser Met Val Tyr Leu Lys Val Gly Asn Glu Thr Arg Lys Tyr Lys Met
                85                  90                  95

Thr Ser Ile Arg Ser Val Lys Pro Thr Asp Val Glu Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Ser Arg Lys Ile Phe Val Ala Thr
130                 135                 140

Glu Val Lys
145

<210> SEQ ID NO 21
<211> LENGTH: 5

```
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 21

Leu Pro Xaa Thr Gly
1               5

<210> SEQ ID NO 22
<211> LENGTH: 5
<212> TYPE: PRT
<213> ORGANISM: Artificial Sequence
<220> FEATURE:
<223> OTHER INFORMATION: sortase recognition motif

<400> SEQUENCE: 22

Leu Pro Glu Thr Gly
1               5

<210> SEQ ID NO 23
<211> LENGTH: 2
<212> TYPE: PRT
<213> ORGANISM: Artificial Sequence
<220> FEATURE:
<223> OTHER INFORMATION: sortase acceptor motif

<400> SEQUENCE: 23

Gly Gly
1

<210> SEQ ID NO 24
<211> LENGTH: 3
<212> TYPE: PRT
<213> ORGANISM: Artificial Sequence
<220> FEATURE:
<223> OTHER INFORMATION: sortase acceptor motif

<400> SEQUENCE: 24

Gly Gly Gly
1

<210> SEQ ID NO 25
<211> LENGTH: 3
<212> TYPE: PRT
<213> ORGANISM: Artificial Sequence
<220> FEATURE:
<223> OTHER INFORMATION: sortase acceptor motif

<400> SEQUENCE: 25

Cys Gly Gly
1

<210> SEQ ID NO 26
<211> LENGTH: 3
<212> TYPE: PRT
<213> ORGANISM: Artificial Sequence
<220> FEATURE:
<223> OTHER INFORMATION: sortase acceptor motif

<400> SEQUENCE: 26

Lys Gly Gly
1
```

```
<210> SEQ ID NO 27
<211> LENGTH: 5
<212> TYPE: PRT
<213> ORGANISM: Artificial Sequence
<220> FEATURE:
<223> OTHER INFORMATION: Arg-tag

<400> SEQUENCE: 27

Arg Arg Arg Arg Arg
1               5

<210> SEQ ID NO 28
<211> LENGTH: 6
<212> TYPE: PRT
<213> ORGANISM: Artificial Sequence
<220> FEATURE:
<223> OTHER INFORMATION: Arg-tag 2

<400> SEQUENCE: 28

Arg Arg Arg Arg Arg Arg
1               5

<210> SEQ ID NO 29
<211> LENGTH: 6
<212> TYPE: PRT
<213> ORGANISM: Artificial Sequence
<220> FEATURE:
<223> OTHER INFORMATION: His-tag

<400> SEQUENCE: 29

His His His His His His
1               5

<210> SEQ ID NO 30
<211> LENGTH: 19
<212> TYPE: PRT
<213> ORGANISM: Artificial Sequence
<220> FEATURE:
<223> OTHER INFORMATION: amino acid tag

<400> SEQUENCE: 30

Lys Asp His Leu Ile His Asn Val His Lys Glu Phe His Ala His Ala
1               5                   10                  15

His Asn Lys

<210> SEQ ID NO 31
<211> LENGTH: 8
<212> TYPE: PRT
<213> ORGANISM: Artificial Sequence
<220> FEATURE:
<223> OTHER INFORMATION: amino acid tag

<400> SEQUENCE: 31

Asp Tyr Lys Asp Asp Asp Asp Lys
1               5

<210> SEQ ID NO 32
<211> LENGTH: 22
<212> TYPE: PRT
<213> ORGANISM: Artificial Sequence
<220> FEATURE:
<223> OTHER INFORMATION: amino acid tag

<400> SEQUENCE: 32

Asp Tyr Lys Asp His Asp Gly Asp Tyr Lys Asp His Asp Ile Asp Tyr
1               5                   10                  15
```

```
Lys Asp Asp Asp Asp Lys
            20

<210> SEQ ID NO 33
<211> LENGTH: 9
<212> TYPE: PRT
<213> ORGANISM: Artificial Sequence
<220> FEATURE:
<223> OTHER INFORMATION: amino acid tag#

<400> SEQUENCE: 33

Ala Trp Arg His Pro Gln Phe Gly Gly
1               5

<210> SEQ ID NO 34
<211> LENGTH: 8
<212> TYPE: PRT
<213> ORGANISM: Artificial Sequence
<220> FEATURE:
<223> OTHER INFORMATION: amino acid tag

<400> SEQUENCE: 34

Trp Ser His Pro Gln Phe Glu Lys
1               5

<210> SEQ ID NO 35
<211> LENGTH: 10
<212> TYPE: PRT
<213> ORGANISM: Artificial Sequence
<220> FEATURE:
<223> OTHER INFORMATION: amino acid tag

<400> SEQUENCE: 35

Met Asp Val Glu Ala Trp Leu Gly Ala Arg
1               5                   10

<210> SEQ ID NO 36
<211> LENGTH: 16
<212> TYPE: PRT
<213> ORGANISM: Artificial Sequence
<220> FEATURE:
<223> OTHER INFORMATION: amino acid tag

<400> SEQUENCE: 36

Met Asp Val Glu Ala Trp Leu Gly Ala Arg Val Pro Leu Val Glu Thr
1               5                   10                  15

<210> SEQ ID NO 37
<211> LENGTH: 38
<212> TYPE: PRT
<213> ORGANISM: Artificial Sequence
<220> FEATURE:
<223> OTHER INFORMATION: amino acid tag

<400> SEQUENCE: 37

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 38
<211> LENGTH: 10
<212> TYPE: PRT
```

-continued

```
<213> ORGANISM: Artificial Sequence
<220> FEATURE:
<223> OTHER INFORMATION: amino acid tag

<400> SEQUENCE: 38

Glu Gln Lys Leu Ile Ser Glu Glu Asp Leu
1               5                   10

<210> SEQ ID NO 39
<211> LENGTH: 15
<212> TYPE: PRT
<213> ORGANISM: Artificial Sequence
<220> FEATURE:
<223> OTHER INFORMATION: amino acid tag

<400> SEQUENCE: 39

Lys Glu Thr Ala Ala Ala Lys Phe Glu Arg Gln His Met Asp Ser
1               5                   10                  15

<210> SEQ ID NO 40
<211> LENGTH: 26
<212> TYPE: PRT
<213> ORGANISM: Artificial Sequence
<220> FEATURE:
<223> OTHER INFORMATION: amino acid tag

<400> SEQUENCE: 40

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 41
<211> LENGTH: 47
<212> TYPE: PRT
<213> ORGANISM: Artificial Sequence
<220> FEATURE:
<223> OTHER INFORMATION: amino acid tag

<400> SEQUENCE: 41

Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
        35                  40                  45

<210> SEQ ID NO 42
<211> LENGTH: 32
<212> TYPE: PRT
<213> ORGANISM: Butyrivibrio fibrisolvens

<400> SEQUENCE: 42

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
            20                  25                  30

<210> SEQ ID NO 43
<211> LENGTH: 51
<212> TYPE: PRT
<213> ORGANISM: Artificial Sequence
<220> FEATURE:
<223> OTHER INFORMATION: chitin-binding-domain
```

```
<400> SEQUENCE: 43

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50

<210> SEQ ID NO 44
<211> LENGTH: 209
<212> TYPE: PRT
<213> ORGANISM: Chondrus crispus

<400> SEQUENCE: 44

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
            20                  25                  30

Arg Val Val Phe Asp His Trp Lys Glu Ala Lys Pro Lys Thr Pro Tyr
        35                  40                  45

Ala Ala Leu Pro Met Leu Thr Val Asp Gly Met Gln Val Ala Gln Ser
    50                  55                  60

Asp Ala Ile Leu Arg Tyr Cys Gly Lys Leu Ala Gly Leu Tyr Pro Ser
65                  70                  75                  80

Asp Pro Leu Glu Ala Ala Lys Val Asp Glu Val Gly Val Ile Asp
                85                  90                  95

Asp Val Thr His Ala Met Tyr Arg Tyr Arg Gly Asp Asp Lys Asp Lys
                100                 105                 110

Leu Arg Glu Glu Arg Asp Lys Phe Ser Lys Val Asp Val Pro Arg Tyr
            115                 120                 125

Val Gly Ala Leu Glu Lys Arg Leu Glu Ala Phe Gly Asp Gly Pro Trp
    130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Asp Lys Asp Leu
                165                 170                 175

Leu Glu Gly Tyr Val Arg Ile Val Lys Ser Tyr Ser Ala Val Met Glu
            180                 185                 190

His Pro Lys Val Thr Glu Trp Tyr Glu Lys Lys Pro Val Lys Met Phe
        195                 200                 205

Ser

<210> SEQ ID NO 45
<211> LENGTH: 396
<212> TYPE: PRT
<213> ORGANISM: Escherichia coli

<400> SEQUENCE: 45

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45
```

Val Gly Lys Lys Phe Glu Lys Asp Thr Gly Ile Lys Val Thr Val Glu
 50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
370                 375                 380

Glu Ala Leu Lys Asp Ala Gln Thr Arg Ile Thr Lys
385                 390                 395

<210> SEQ ID NO 46
<211> LENGTH: 206
<212> TYPE: PRT
<213> ORGANISM: Staphylococcus aureus

<400> SEQUENCE: 46

Met Lys Lys Trp Thr Asn Arg Leu Met Thr Ile Ala Gly Val Val Leu
 1               5                  10                  15

Ile Leu Val Ala Ala Tyr Leu Phe Ala Lys Pro His Ile Asp Asn Tyr

```
                20                  25                  30
Leu His Asp Lys Asp Lys Asp Glu Lys Ile Glu Gln Tyr Asp Lys Asn
                35                  40                  45

Val Lys Glu Gln Ala Ser Lys Asp Lys Gln Ala Lys Pro Gln
 50                  55                  60

Ile Pro Lys Asp Lys Ser Lys Val Ala Gly Tyr Ile Glu Ile Pro Asp
 65                  70                  75                  80

Ala Asp Ile Lys Glu Pro Val Tyr Pro Gly Pro Ala Thr Pro Glu Gln
                 85                  90                  95

Leu Asn Arg Gly Val Ser Phe Ala Glu Glu Asn Glu Ser Leu Asp Asp
                100                 105                 110

Gln Asn Ile Ser Ile Ala Gly His Thr Phe Ile Asp Arg Pro Asn Tyr
                115                 120                 125

Gln Phe Thr Asn Leu Lys Ala Ala Lys Lys Gly Ser Met Val Tyr Phe
                130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
                180                 185                 190

Val Trp Glu Lys Arg Lys Ile Phe Val Ala Thr Glu Val Lys
                195                 200                 205

<210> SEQ ID NO 47
<211> LENGTH: 4
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=any amino acid residue except P

<400> SEQUENCE: 47

Leu Pro Xaa Thr
1

<210> SEQ ID NO 48
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=D, E, A, N, Q, K, R
<220> FEATURE:
<221> NAME/KEY: MISC_FEATURE
<222> LOCATION: (5)..(5)
<223> OTHER INFORMATION: X=A,G

<400> SEQUENCE: 48

Leu Pro Xaa Thr Xaa
1               5

<210> SEQ ID NO 49
<211> LENGTH: 5
<212> TYPE: PRT
<213> ORGANISM: Artificial Sequence
<220> FEATURE:
```

<223> OTHER INFORMATION: sortase recognition motif
<220> FEATURE:
<221> NAME/KEY: MISC_FEATURE
<222> LOCATION: (3)..(3)
<223> OTHER INFORMATION: X=D, E, A, N, Q, K, R

<400> SEQUENCE: 49

Leu Pro Xaa Thr Ala
1               5

<210> SEQ ID NO 50
<211> LENGTH: 5
<212> TYPE: PRT
<213> ORGANISM: Artificial Sequence
<220> FEATURE:
<223> OTHER INFORMATION: sortase recognition motif
<220> FEATURE:
<221> NAME/KEY: MISC_FEATURE
<222> LOCATION: (3)..(3)
<223> OTHER INFORMATION: X=D, E, A, N, Q, K, R

<400> SEQUENCE: 50

Leu Pro Xaa Thr Gly
1               5

<210> SEQ ID NO 51
<211> LENGTH: 12
<212> TYPE: PRT
<213> ORGANISM: Artificial Sequence
<220> FEATURE:
<223> OTHER INFORMATION: purification tag

<400> SEQUENCE: 51

Met Arg Gly Ser His His His His His His Gly Ser
1               5                   10

<210> SEQ ID NO 52
<211> LENGTH: 148
<212> TYPE: PRT
<213> ORGANISM: Artificial Sequence
<220> FEATURE:
<223> OTHER INFORMATION: mutated Sortase from US 9,267,127

<400> SEQUENCE: 52

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Arg Glu Gln Leu Asn Arg Gly Val Ser Phe Ala Glu Glu
        35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
                100                 105                 110

```
Glu Gln Lys Gly Lys Asp Lys Gln Leu Thr Leu Ile Thr Cys Asp Asp
        115                 120                 125

Tyr Asn Glu Glu Thr Gly Val Trp Glu Lys Arg Lys Ile Phe Val Ala
        130                 135                 140

Thr Glu Val Lys
145
```